United States Patent [19]

Hallinan et al.

[11] Patent Number: 5,182,272
[45] Date of Patent: Jan. 26, 1993

[54] 8-SUBSTITUTED-DIBENZ[B,F][1,4]OXAZE-PINE-10(11)-CARBOXYLIC ACID, SUBSTITUTED HYDRAZIDES, PHARMACEUTICAL COMPOSITIONS, AND METHODS FOR TREATING PAIN

[75] Inventors: E. Ann Hallinan, Evanston; Robert K. Husa; Karen B. Peterson, both of Vernon Hills, all of Ill.

[73] Assignee: G. D. Searle & Co., Chicago, Ill.

[21] Appl. No.: 695,489

[22] Filed: May 3, 1991

[51] Int. Cl.[5] ............... C07D 267/20; C07D 281/16; C07F 9/6561; A61K 31/55

[52] U.S. Cl. ............................. 514/80; 514/211; 540/542; 540/547

[58] Field of Search ............. 540/542, 547; 514/80, 514/211

[56] References Cited

U.S. PATENT DOCUMENTS

| | | | |
|---|---|---|---|
| 3,534,019 | 10/1970 | Coyne et al. | 260/239 |
| 3,624,104 | 11/1971 | Cusic et al. | 260/333 |
| 3,917,649 | 11/1975 | Mueller | 260/333 |
| 3,989,719 | 11/1976 | Mueller | 260/333 |
| 3,992,375 | 11/1976 | Mueller | 260/333 |
| 4,045,442 | 8/1977 | Mueller | 260/293.58 |
| 4,125,532 | 11/1978 | Mueller | 260/244.4 |
| 4,170,593 | 10/1979 | Mueller | 260/243.3 |
| 4,559,336 | 12/1985 | Mueller | 514/211 |
| 4,559,337 | 12/1985 | Mueller | 514/211 |
| 4,614,617 | 9/1986 | Mueller | 540/547 |

FOREIGN PATENT DOCUMENTS

| | | |
|---|---|---|
| 0012385 | 6/1980 | European Pat. Off. |
| 0193822 | 9/1986 | European Pat. Off. |
| 0218077 | 4/1987 | European Pat. Off. |
| 6700603 | 7/1967 | Netherlands |
| 1170322 | 11/1969 | United Kingdom |
| 1331892 | 9/1973 | United Kingdom |
| 1522003 | 8/1978 | United Kingdom |

OTHER PUBLICATIONS

Drower, et al., "The Antiociceptive Effects of Prostaglandin Antagonists in the Rat," *European Journal of Pharmacology*, 133, 249–256 (1987).

J. H. Sanner, "Dibenzoxapzepine Hydrazides as Prostaglandin Antagonists," *Intra-Science Chem. Rept.*, vol. 6, No. 1, 1–9 (1972).

K. Nagarajan, et al., "Synthesis of 10,11-Dihydrodibenz[b,f][1,4]oxazepine Derivatives as Potential Anticonvulsants & Psychotropic Agents" *Indian Journal of Chemistry*, vol. 24B, 840–844 (1985).

D. E. MacIntyre, et al., "Antagonism of Human Platelet Responses to Stimulatory and Inhibitory Prostaglandins," *Prog. Lipid. Res. 20* (1–4), 453–9 (1981).

R. Gimet, et al., "Quantitative Determination of Polymorphic Forms in a Formulation Matrix Using the Near Infra-Red Reflectance Analysis Technique," *J. Pharmaceutical & Biomedical Analysis*, vol. 5, No. 3, 205–211 (1987).

J. H. Sanner, et al., "Structure-Activity Relationships of some Dibenzoxazepine Derivatives as Prostaglandin Antagonists," *Advances in the Biosciences*, 9, 139–148 (1972).

A. Rakovska, et al., "Antagonistic Effect of SC-19220 on the Responses of Guinea-Pig Gastric Muscles to Prostaglandins $E_1$, $E_2$ and $F_2$," *Arch. Int. Pharmacodyn.*, 268, 59–69 (1984).

(List continued on next page.)

Primary Examiner—Mukund J. Shah
Assistant Examiner—Philip I. Datlow
Attorney, Agent, or Firm—Roberta L. Hastreiter; Paul D. Matukaitis

[57] ABSTRACT

The present invention provides substituted dibenzoxazepine compounds of Formula I:

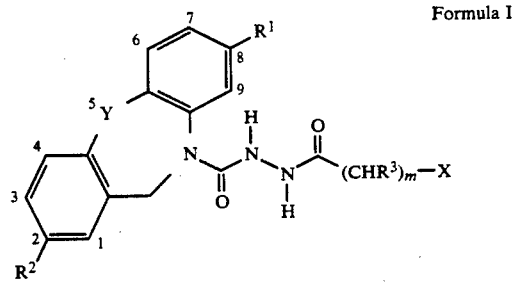

wherein X is

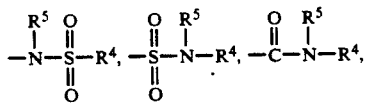

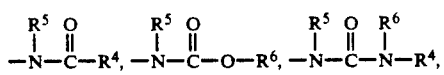

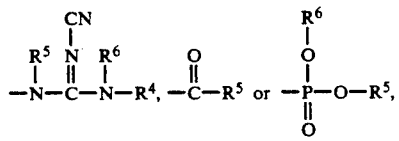

which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

28 Claims, No Drawings

OTHER PUBLICATIONS

W. E. Coyne, et al., "Anticonvulsant Semicarbazides," *J. Med. Chem.*, 11(6), 1158–1160 (1968).

K. Gyires, et al., "The Use of the Writhing Test in Mice for Screening Different Types of Analgesics," *Arch. Int. Pharmacodyn.*, 267, 131–140 (1984).

A. Bennett, et al., "Antagonism of Prostanoid-Induced Contractions of Rat Gastric Fundus Muscle by SC-19220, Sodium Meclofenamate, Indomethacin or Trimethoquinol," *Br. J. Pharmac.*, 71, 169–175 (1980).

C. A. Maggi, et al., "The Effect of SC-19220, a Prostaglandin Antagonist, on the Micturition Reflex in Rats," European Journal of Pharmacology, 152, 273–279 (1988).

George, et al., "Antagonism of Alcohol Hypnosis by Blockage of Prostaglandin Synthesis and Activity: Genotype and Time Course Effects," *Pharmacology Biochemistry & Behavior*, vol. 19, 131–136 (1983).

S. Nakajyo, et al., "Inhibitory Effect of Bassianolide, A Cyclodepsipeptide, on Drug-Induced Contractions of Isolates Smooth Muscle Preparations," *Japan. J. Pharmacol.*, 32, 55–64 (1982).

A. Gomes, et al., "Pharmacodynamics of Venom of the Centipede *Scolopendra subspinipes dehaani*," Indian Journal of Experimental Biology, vol. 20, 615–618 (1982).

8-SUBSTITUTED-DIBENZ[B,F][1,4]OXAZEPINE-10(11)-CARBOXYLIC ACID, SUBSTITUTED HYDRAZIDES, PHARMACEUTICAL COMPOSITIONS, AND METHODS FOR TREATING PAIN

BACKGROUND OF THE INVENTION (1) Field of the Invention

The present invention generally relates to compounds having pharmacological activity which are useful as pharmacological agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

Description of the Related Art

U.S. Pat. Nos. 4,559,336 and 4,614,617 (a continuation-in-part of U.S. Pat. No. 4,559,336) disclose 8-chlorodibenz[b,f][1,4-]-oxazepine-10(11H)-carboxylic acid, 2-(sulfinyl- and sulfonyl-containing acyl)hydrazides, and intermediates thereof.

U.S. Pat. No. 3,534,019 discloses hydrazides of dibenzoxazepine-, dibenzothiazepine- and dibenzodiazepinecarboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazine compounds.

U.S. Pat. Nos. 4,045,442, 4,125,532 (a divisional of U.S. Pat. Nos. 4,045,442) and 4,170,593 (a divisional of U.S. Pat. No. 4,125,532) disclose 1-(substituted amino)alkanoyl-2-(dibenzoxazepine-10-carbonyl)hydrazine compounds.

U.S. Pat. No. 4,559,337 discloses 8-chlorodibenz[b,f][1,4]-oxazepine-10(11H)-carboxylic acid, 2-(alkoxy-containing acyl)hydrazide compounds.

GB 1 522 003 discloses 1-acyl-2-(8-chloro-10,11dihydrodibenz[b,f][1,4]oxazepine-10-carbonyl)hydrazine compounds.

GB 1 331 892 discloses derivatives of dibenzoxazepine N-carboxylic acid hydrazides.

European patent Application publication No. 0 193 822 discloses 8-chlorodibenz[b,f][1,4]-oxazepine-10(11H)-carboxylic acid, 2-(thio-, sulfinyl- and sulfonyl-containing acyl)hydrazide compounds.

European patent Application publication No. 0 218 077 discloses 8-chlorodibenz[b,f][1,4]oxazepine-10(11H)-carboxylic acid, 2-[(substituted phenylsulfinyl)alkanoyl]hydrazide compounds and 8-chlorodibenz[b,f][1,4]oxazepine-10(11H)-carboxylic acid, 2-[(substituted phenylsulfonyl)alkanoyl]hydrazide compounds, and intermediates used in the preparation of these compounds.

Drower et al., "The Antiociceptive Effects of prostaglandin Antagonists in the Rat," *European Journal of Pharmacology*, 133, 249–256 (1987), disclose the study of the antinociceptive properties of two competitive antagonists of prostaglandins of the E series, 8-chlorodibenz[b,f][1,4]-oxazepine-10(11H)-carboxylic acid, 2-acetylhydrazide and 8-chlorodibenz[b,f][1,4]-oxazepine-10(11H)-carboxylic acid, 2-(5-chloro-1-oxopentyl)hydrazide.

J. H. Sanner, "Dibenzoxazepine Hydrazides as Prostaglandin Antagonists," *Intra-Science Chem. Rept.*, 6(1), 1–9 (1972), describes experiments performed with two dibenzoxazepine derivatives designated SC-18637 and SC-19220, and shown below, and found that SC-18637 and SC-19220 inhibit the stimulant actions of prostaglandins on isolated smooth muscle preparations.

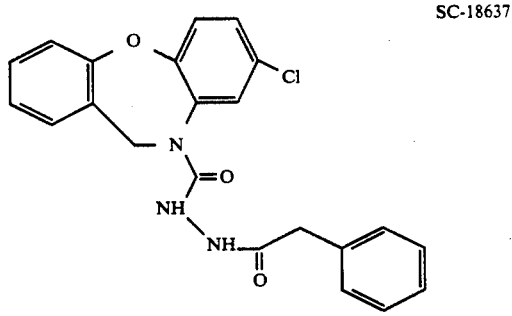

SC-18637

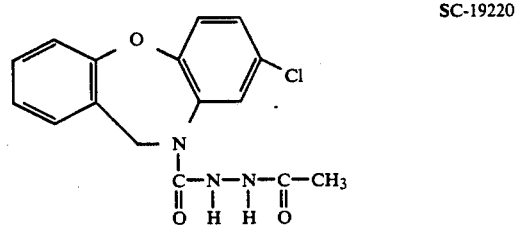

SC-19220

K. Nagarajan et al., "Synthesis of 10,11-Dihydrodibenz[b,f][1,4]oxazepine Derivatives as potential Anticonvulsants & Psychotropic Agents," *Indian Journal of Chemistry*, 24B, 840–844 (1985), disclose the synthesis of acyl, carbamoyl and thiocarbamoyl derivatives of 10,11-dihydrodibenz[b,f][1,4]oxazepine, most of which have either a nitro or an amino group at position-2, as analogues of carbamazepine, and the evaluation of these derivatives as anticonvulsants associated with neuroleptic activity.

Other art which relates to the present invention includes that which is discussed below.

D. E. MacIntyre et al., "Antagonism of Human Platelet Responses to Stimulatory and Inhibitory Prostaglandins," *Prog. Lipid. Res.*, 20(1-4), 453-9 (1981), disclose on page 454, Lines 11-12, Page 458, Lines 43-44, and in Table 1, two dibenzoxazepine compounds designated SC-19220 and SC-25191, and shown above and below, respectively, which were employed in an investigation of the effects of prostaglandin antagonists on platelet responses to stimulatory and inhibitory prostaglandins.

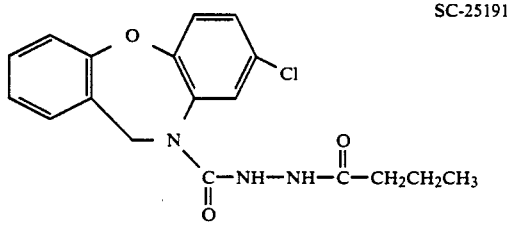

R. Gimet et al., "Quantitative Determination of polymorphic Forms in a Formulation Matrix Using the Near Infra-Red Reflectance Analysis Technique," *J. Pharmaceutical & Biomedical Analysis*, 5(3), 205-211 (1987), disclose an analytical method for the determination of the polymorphic transformation of an active ingredient in a solid dosage form matrix, and discuss a compound designated SC-25469, and shown below, at page 206, Lines 16-23.

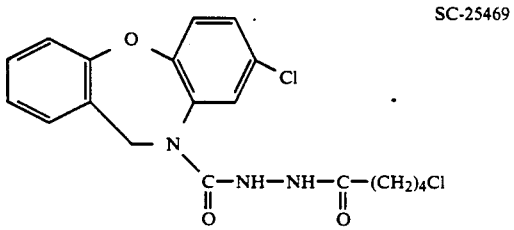

J. H. Sanner et al., "Structure-Activity Relationships of some Dibenzoxazepine Derivatives as Prostaglandin Antagonists," *Advances in the Biosciences*, 9, 139-148 (1972), disclose tests for prostaglandin antagonism on isolated guinea-pig ileum and rat stomach fundus strips with the n-butanoyl, i-butanoyl and n-hexanoyl analogs of SC-19220 (see structure above) and, on Page 140, Lines 11-18, show the chemical structures of the compounds used in the study.

A. Rakovska et al., "Antagonistic Effect of Sc-19220 on the Responses of Guinea-Pig Gastric Muscles to Prostaglandins $E_1$, $E_2$ and $F_2$," *Arch. int. Pharmacodyn*, 268, 59-69 (1984), disclose a study of the contractile responses of guinea-pig gastric muscles to SC-19220 (see structure above), and the prostaglandin-blocking activity and specificity of SC-19220 on these muscles.

W. E. Coyne et al., "Anticonvulsant Semicarbazides," *J. Med. Chem.*, 11(6), 1158-1160 (1968), disclose the investigation of the structure-activity relationship of the anticonvulsant activity of a series of semicarbazides which was synthesized from various tricyclic amines (see Table I, Page 1160).

K. Gyires et al., "The Use of the Writhing Test in Mice for Screening Different Types of Analgesics," *Arch. int. Pharmacodyn*, 267, 131-140 (1984), describe a comparison of the analgesic potency of some prostaglandin synthesis inhibitors, including SC-19220 (see structure above), and morphine using the writhing test. SC-19220 is discussed on page 133, Lines 10 and 14-16, in Table II (page 134), and on Page 135, Lines 16-25, and page 137, Lines 34-38.

A. Bennett et al., "Antagonism of Prostanoid-Induced contractions of Rat Gastric Fundus Muscle by SC-19220, Sodium Meclofenamate, Indomethacin or Trimethoquinol," *Br. J. Pharmac*, 71, 169-175 (1980), disclose the study of the effects of several compounds, including SC-19220 (see structure above), on contractions of the rat stomach longitudinal muscle to several prostanoids. SC-19220 is discussed on page 175, Paragraph 1, Page 170, Paragraph 4, in Table 1 and FIG. 2, on Page 172, Paragraph 2, and on page 174, Paragraphs 1 and 2.

C. A. Maggi et al., "The Effect of SC-19220, a Prostaglandin Antagonist, on the Micturition Reflex in Rats," *European Journal of Pharmacology*, 152, 273-279 (198), disclose a study in which Sc-19220 (see structure above) is said to have increased the bladder capacity and reduced the voiding efficiency of micturition of urethane-anesthetized rats.

George et al., "Antagonism of Alcohol Hypnosis by Blockade of Prostaglandin Synthesis and Activity: Genotype and Time Course Effects," *Pharmacology Biochemistry & Behavior*, 19, 131-136 (1983), disclose a study of genetic and time-course factors of the effect of the antagonism of alcohol-induced behaviors of mice which have been pretreated with prostaglandin synthetase inhibitors and the effect of Sc-19220 (see structure above) on ethanol sleep time.

S. Nakajyo et al., "Inhibitory Effect of Bassianolide, A Cyclodepsipeptide, on Drug-Induced Contractions of Isolates Smooth Muscle Preparations," *Japan. J. Pharmacol.*, 32, 55-64 (1982), disclose a study of the effect of bassianolide on the contractile responses induced by various types of neurotransmitters and autacoids. SC-19220 (see structure above) was employed in this study and is discussed on page 57, Paragraph 1, in FIGS. 2 and 3, in Table 1, and on Page 60, Paragraph 1, Page 62, Paragraph 3, and Page 63, Paragraph 2.

A. Gomes et al., "Pharmacodynamics of Venom of the Centipede Scolopendra subspinipes dehaani." *Indian Journal of Experimental Biology*, 20, 615-618 (1982), disclose an investigation of the pharmacodynamic actions of the venom of the tropical centipede *S. subsoinioes*. SC-19220 (see structure above) was employed in this study and is discussed on Page 615 (abstract), Page 616, Line 30, Page 617, Lines 13-18, in FIGS. 4 and 5, and on page 618, Lines 23-26.

Each of the documents described hereinabove discloses compounds which are structurally different from the compounds of the present invention. Thus, the compounds of the present invention are structurally distinct from that which has been described in the art.

Compounds of the present invention have been found to exhibit activity as prostaglandin $E_2$ antagonists. Some of these compounds were surprisingly and unexpectedly found to be more than three to four times more effective as prostaglandin $E_2$ antagonists than prostaglandin antagonists reported in the literature.

Moreover, compounds within the present invention were surprisingly and unexpectedly found to be water soluble. Thus, these compounds may be much more easily formulated into compositions which are suitable for oral, parenteral and other modes of administration than similar compounds which are not water soluble.

SUMMARY OF THE INVENTION

The present invention provides compounds comprising a structure of Formula I:

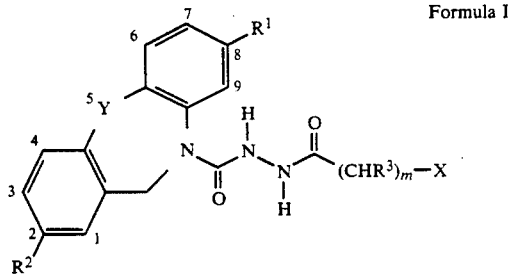

Formula I or a pharmaceutically-acceptable salt, ester or amide thereof, wherein:

Y is: oxygen, sulfur,

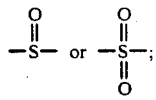

$R^1$ is: hydrogen, halogen or $-CF_3$;

$R^2$ is: hydrogen, halogen, $-OH$ or $-OCH_3$;

$R^3$ is: hydrogen, alkyl, aryl, alkyl-substituted aryl or aryl-substituted alkyl;

m is: an integer of from 1 to 5;

X is:

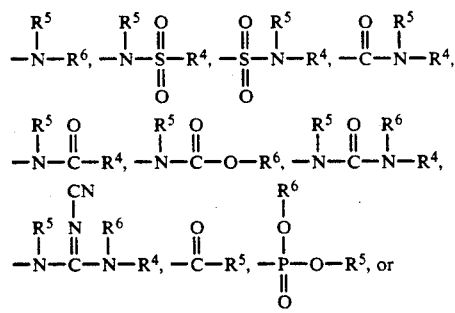

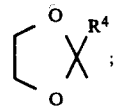

$R^4$ is: hydrogen, alkyl, aryl, alkyl-substituted aryl, trifluormethyl-substituted aryl or aryl-substituted alkyl; and $R^5$ and $R^6$ are: each independently hydrogen, alkyl, aryl, alkyl-substituted aryl or aryl-substituted alkyl.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The term "alkyl" as used herein means a saturated hydrocarbon radical having from one to ten carbon atoms, which can be a straight or branched chain, and which may be unsubstituted or halo-substituted. Representative of such radicals are methyl, trifluoromethyl, ethyl, n-propyl, isopropyl, n-butyl, sec-butyl, isobutyl, tert-butyl, 2-ethylhexyl, n-octyl, 2,4-dimethylpentyl and the like.

The phrase "alkyl-substituted aryl" as used herein means an aryl radical, as defined below, having one or more hydrogen atoms replaced by an alkyl radical, as defined above, for example N-methylpyrrolyl.

The term "aryl" as used herein means 5- and 6-membered single-ring aromatic radicals which may include from zero to four heteroatoms. Representative aryls include (phenyl, thienyl, furanyl, pyridinyl, imidazolyl, pyrimidyl, (is)oxazolyl, thiazolyl, triazolyl, tetrazolyl, pyrrolyl) and the like.

The phrase "aryl-substituted alkyl" as used herein means an alkyl radical, as defined above, having one or more hydrogen atoms replaced by an aryl radical, as defined above.

The term "analgesia" as used herein means the reduction, or absence, of sensibility to pain, designating particularly the relief of pain without loss of consciousness.

The term "animal" as used herein includes humans and animals.

The term "benzyl" as used herein means the group $C_6H_5CH_2-$.

The abbreviation "Boc" as used herein means t-butyloxycarbonyl.

The abbreviation "Bzl" as used herein means benzyl.

The term "composition" as used herein means a product which results from the combining of more than one ingredient.

The phrase "$ED_{50}$ dose" as used herein means that dose of a compound or drug which produced a biological effect, such as producing analgesia, in 50% of the animals to which the compound or drug was administered.

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "i.g." as used herein means that a compound or drug was administered intragastrically, as defined below.

The term "intragastrically" as used herein means that a compound or drug was administered into the stomach.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts and alkali metal salts such as sodium and potassium and alkaline earth salts, such as calcium and magnesium.

The term "phenyl" as used herein means the group $C_6H_5—$, derived from benzene.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "s.c." as used herein means that a compound or drug was administered subcutaneously.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

(2) Description of Invention

In one aspect, the present invention provides compounds comprising a structure of Formula I, as described above, and pharmaceutically-acceptable salts, esters and amides thereof.

The compounds of the present invention comprise a class of substituted dibenzoxazepine compounds in which the 2-, 5-, and/or 8-position, and/or the side chain, is substituted. Such compounds have been shown to exhibit activity as prostaglandin $E_2$ antagonists.

Specific compounds within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans- geometric isomers, R-and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66:1-19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, and methods for treating central nervous disorders, including convulsions and ischemia, and asthma, enuresis, arrhythmia, diarrhea, dysmenorrhea and osteoporosis in an animal, comprising administering a therapeutically-effective amount of a compound of Formula I, as described hereinabove, to the animal.

The most preferred embodiment of the present invention is the compound described in Example 20 below.

(3) Utility

Compounds of the present invention exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals. In addition to treating pain, these compounds and compositions would be useful in treating convulsions, ischemia and other central nervous system disorders, as well as osteoporosis, dysmenorrhea, asthma, enuresis, arrhythmia and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily-available starting materials, reagents and conventional synthesis procedures. Unless otherwise specified, the various substituents of the compounds and materials present in the general reaction schemes are defined in the same manner as they are defined above in Formula I.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

GENERAL REACTION SCHEME NO. 1

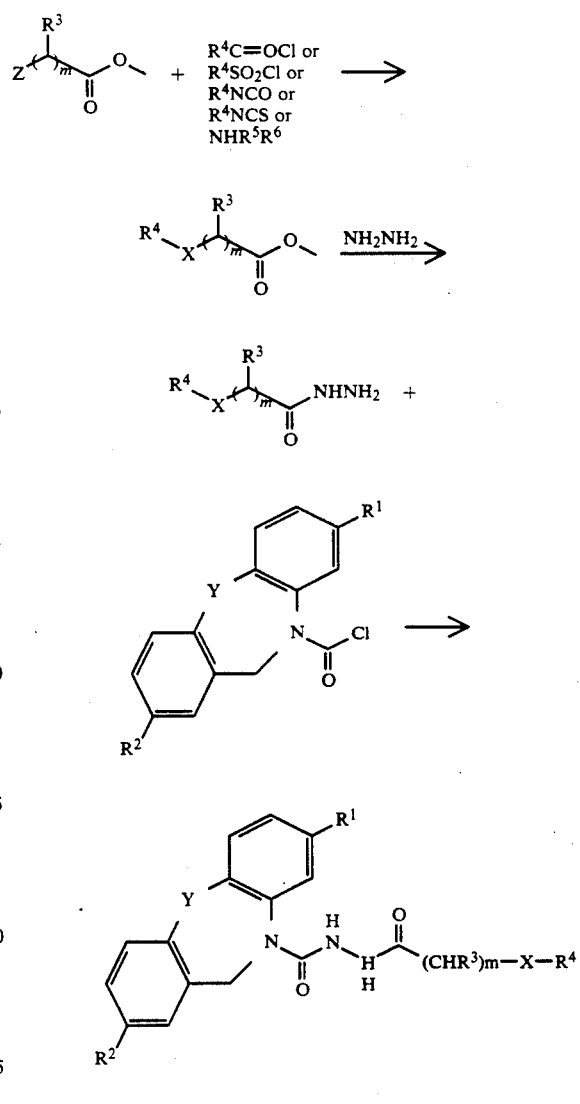

$Z = NH_2, NHR^5, SO_2Cl, C=OCl$

GENERAL REACTION SCHEME NO. 2
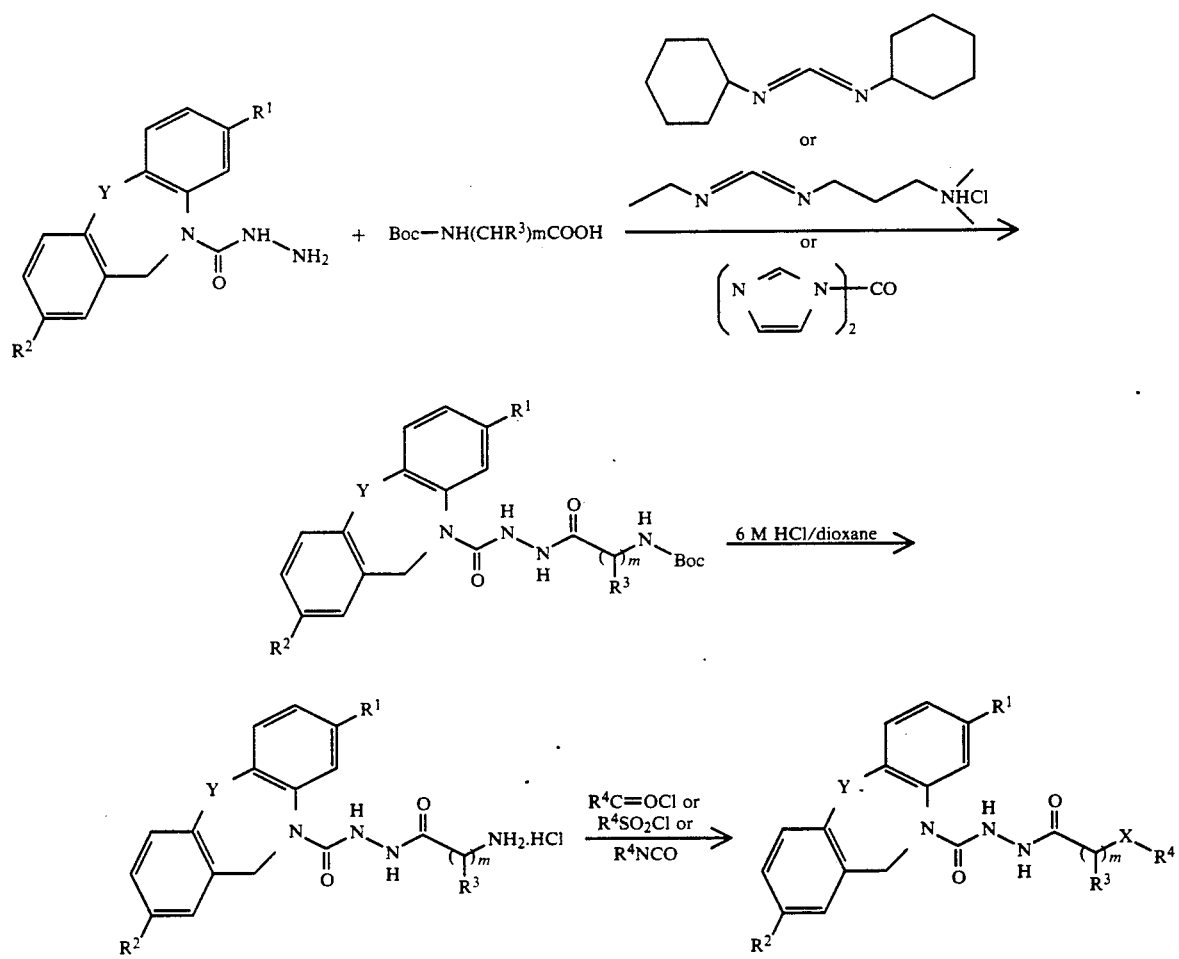
GENERAL REACTION SCHEME NO. 3
-continued
GENERAL REACTION SCHEME NO. 3
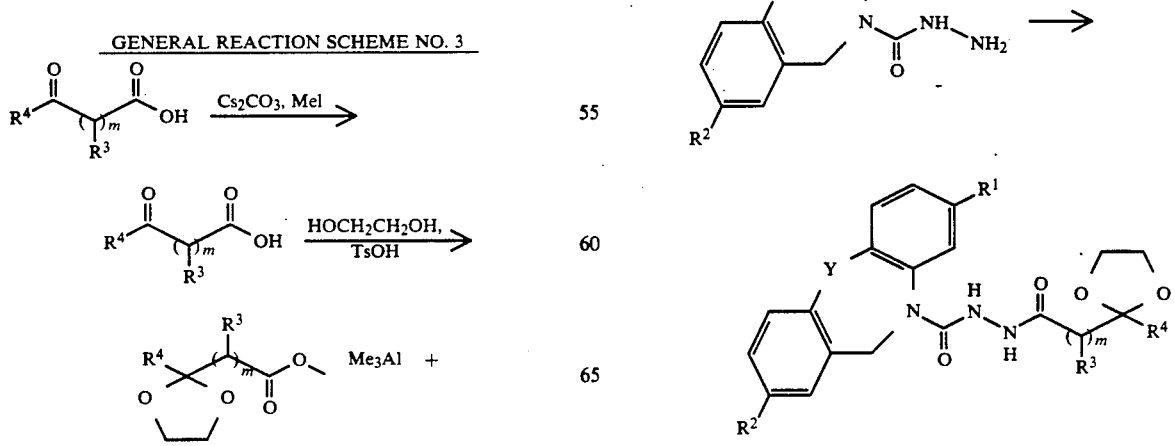

GENERAL REACTION SCHEME NO. 4

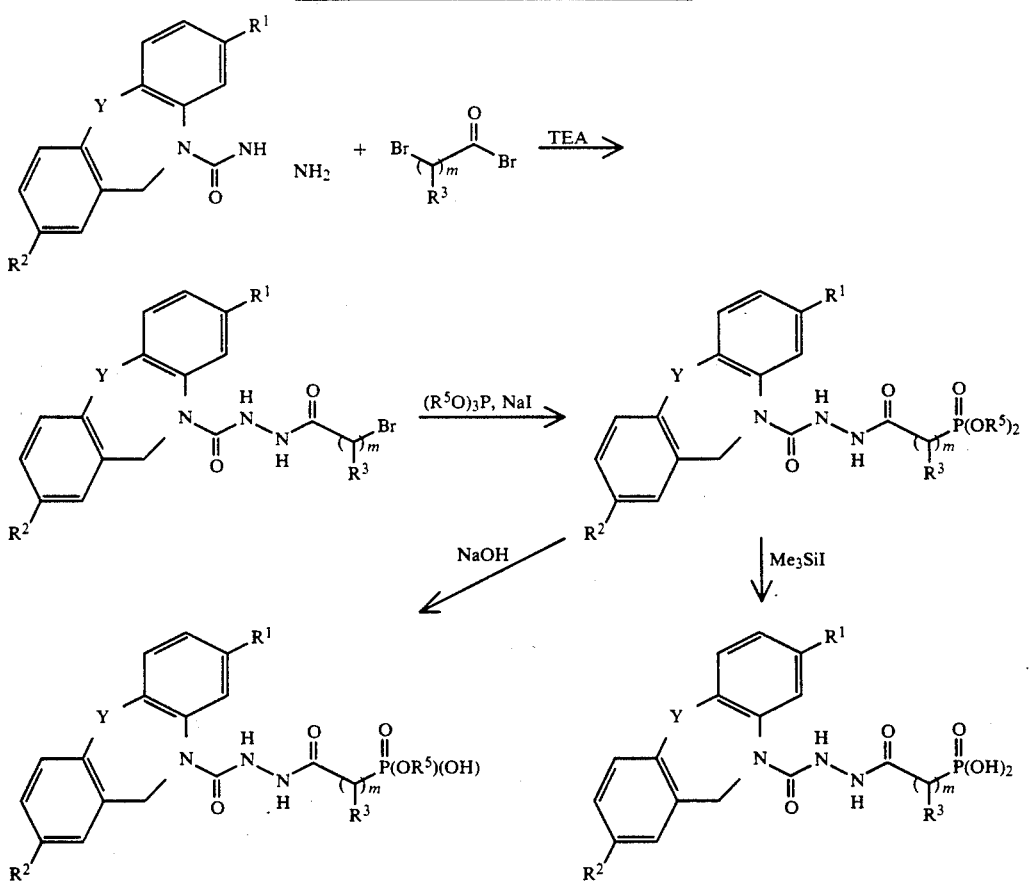

GENERAL REACTION SCHEME NO. 5

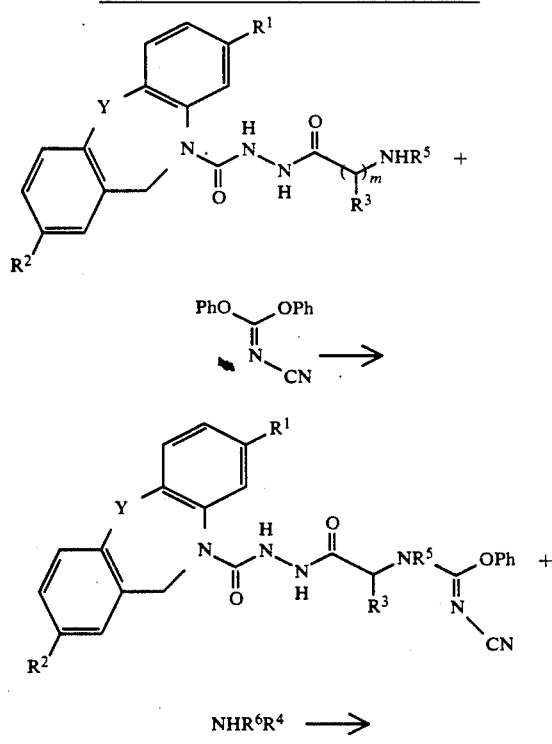

-continued
GENERAL REACTION SCHEME NO. 5

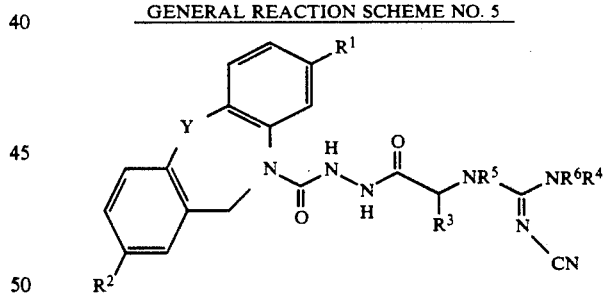

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a particular patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the present invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound (a compound of Formula I) per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile, injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically-acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the present invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms ar made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All starting materials used in the examples are commercially available. Most of the starting materials were obtained from Aldrich Chemical Co., Milwaukee, Wis.

The abbreviation "Me" as used in some of the chemical structures presented in the examples, and in other parts of this specification, means methyl ($-CH_3$).

All patents and publications referred to in the examples, and throughout the specification, are hereby incorporated herein by reference, without admission that such is prior art.

EXAMPLE 1

8-chlorodibenz[b.f][1,4]oxazepine-10(11H)-carboxylic acid, hydrazide (1)

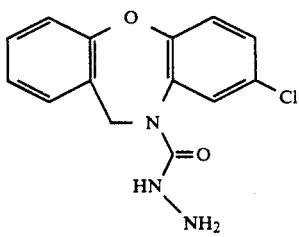

8-chlorodibenz[b,f][1,4]oxazepine-10(11H)-carboxylic acid, hydrazide (1) was synthesized in the manner described in U.S. Pat. No. 3,534,019.

To a solution of 7.3 parts of 100% hydrazine hydrate in 40 parts of ethanol was added, at 5°-10° C. with stirring, a solution of 13.0 parts of 8-chlorodibenz[b,f][1,4]-oxazepine-10(11H)-carbonyl chloride (2) in 200 parts by volume of a 1:1 ether-methylene chloride solution. When the addition was complete, the mixture was allowed to warm to room temperature and was stirred for 1 hour. The mixture was then filtered and the solvent was evaporated from the filtrate. The resultant residue was then dissolved in chloroform, and the resulting chloroform solution was washed with water and dried over magnesium sulfate. The chloroform solvent was then evaporated, and the resultant crude residue was triturated with petroleum ether to give a white solid, which was then recrystallized from ethanol.

EXAMPLE 2

8-chlorodibenz[(b.f]1[1,4]-oxazepine-10(11H)-carbonyl chloride (2)

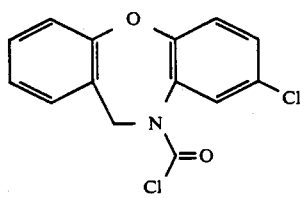

8-chlorodibenz[b,f][1,4]-oxazepine-10(11H)-carbonyl chloride (2) was also synthesized in the manner described in U.S. Pat. No. 3,534,019.

13 parts of phosgene in 45 parts of toluene was stirred for hours at 5°-10° C., and then 70 parts of ether was added. This was followed by the addition of a solution of 18.9 parts of 8-chloro-10,11-dihydrodibenz[b,f][1,-4]oxazepine and 7.2 parts of triethylamine in 140 parts of ether. After the addition was complete, the mixture was stirred for 2 hours, and then was filtered. The solvent was then evaporated from the filtrate. The resulting residue was then dissolved in 200 parts by volume of hot hexane, and this mixture was then filtered and cooled.

EXAMPLE 3

N-(2-thienylacetyl)-β-alanine, methyl ester (3)

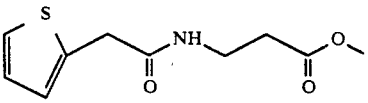

To an ice-bath-cooled solution of 0.45 g (3.2 mmol) of methyl β-alaninate hydrochloride and 1.14 mL of N,N-diisopropylethylamine (DIEA) in 10 mL of dimethylformamide (DMF) was added dropwise a 2 mL DMF solution of 0.51 g (3.2 mmol) of 2-thiopheneacetyl chloride. After 16 hours of stirring at room temperature, the reaction mixture was added to 50 mL of ethyl acetate (EtOAc) and 50 mL of 1 M KHSO$_4$, and the resulting layers were separated. The organic layer was washed with 2×50 mL of 1 M KHSO$_4$, 2×50 mL of a saturated KHCO$_3$ solution, and 2×50 mL of H$_2$O. The organic layer was then dried over Na$_2$SO$_4$ (anhydrous), filtered, and then concentrated under reduced pressure.

The resulting residue was purified by column chromatography in the manner described by Still et al., "A Rapid Chromatographic Technique for Preparative Separations with Moderate Resolution," *J. Org. Chem*, 43, 2923 (1978). The yield of N-(2-thienylacetyl)-β-alanine, methyl ester (3) was 0.21 g (29%). The identity and purity of this material, and that of the materials described in the subsequent examples, were confirmed by $^1$H NMR, $^{13}$C NMR, microanalysis, and high performance liquid chromatography (HPLc). Analysis calculated for C$_{10}$H$_4$NO$_3$S (M.W. 228.29): C, 52.61; H, 6.18; N, 6.14. Found: C, 52.84; H, 5.71; N, 6.11.

EXAMPLE 4

N-(2-thienylacetyl)-8-alanine, hydrazide (4)

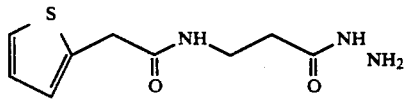

To a 1 mL 2B ethanol (EtOH) solution of 0.11 g (0.5 mmol) of N-(2-thienylacetyl)-β-alanine, methyl ester (3), prepared as described in Example 3 above, in ethanol was added 0.05 g (1 mmol) of hydrazine hydrate. After refluxing for 24 hours, an additional 0.10 g (2 mmol) of hydrazine hydrate was added to the reaction, and the refluxing was continued for 24 hours. The solvent was then removed by aspirator vacuum, and the resulting N-(2-thienylacetyl)-β-alanine, hydrazide (4) was employed immediately in the procedure described in Example 5 below.

EXAMPLE 5

8-chlorodibenz[b,f][1,4]oxazepine-10(11H)-carboxylic acid, 2-[1-oxo-3-(2-thienylacetyl)amino]propyl]hydrazide (5)

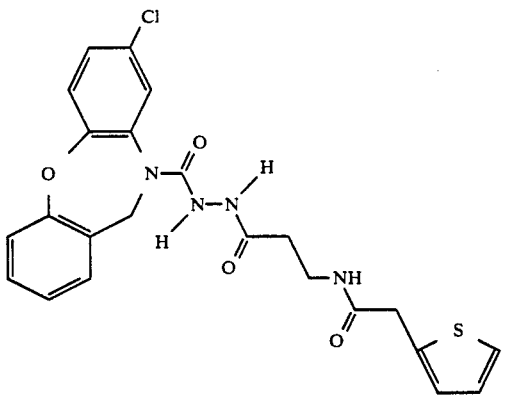

To a stirring 5 mL toluene solution of 0.11 g (0.5 mmol) of N-(2-thienylacetyl)-β-alanine, hydrazide (4), prepared as described above in Example 4, and 0.07 mL (0.5 mmol) of triethylamine (TEA), was added dropwise a 5 mL toluene solution of 0.15 g (o.5 mmol) of 8-chlorodibenz[b,f][1,4]-oxazepine-10(11H)-carbonyl chloride (2), prepared as described above in Example 2. The reaction was heated at reflux for 1 hour, and then the solvent Was removed under vacuum.

The resulting residue was purified by column chromatography in the manner described in Example 3 above to yield 0.16 g (67%) of 8-chlorodibenz-[b,f][1,4]-oxazepine-10(11H)-carboxylic acid, 2-[1-oxo-3-[1-oxo-2-(2-thienyl)ethylamino]propyl]hydrazide (5). Analysis calculated for $C_{23}H_{21}N_4O_4SCl$ 0.25 $H_2O$ (M.W. 489.46): C, 56.44; H, 4.43; N, 11.45. Found: C, 56.28; H, 4.43; N, 11.34.

EXAMPLE 6

N-[(1,1-dimethylethoxy)carbony)]-β-alanine (6)

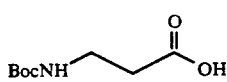

To a stirring solution of 20 g (224 mmol) of β-alanine and 448 mL of N NaoH in 50 mL t-butanol (t-BuOH) was added 73 g (336 mmol) of di-t-butyldicarbonate. After 16 hours, the t-BuOH was removed under water aspirator vacuum, and the reaction mixture was adjusted to pH 4 with M $KHSO_4$. The reaction mixture was then extracted with 3×400 mL EtoAc. The organic layer was dried over $Na_2SO_4$ anhydrous, filtered, and then concentrated in vacuo. A white solid was collected and dried in a steam cabinet. A yield of 41.6 g (98%) of N-[(1,1-dimethylethoxy)carbonyl]-β-alanine (6) was isolated. Analysis calculated for $C_8H_{15}NO_4$ (M.W. 189.21): C, 50.78; H, 7.99; N, 7.40. Found: C, 50.67; H, 7.82; N, 7.44.

EXAMPLE 7

8-chlorodibenz[b,f][1.4]oxazepine-10(11H)-carboxylic acid, 2-(3-[[(1,1-dimethylethoxy)carbonyl]amino]-1-oxopropyl]hydrazide (7)

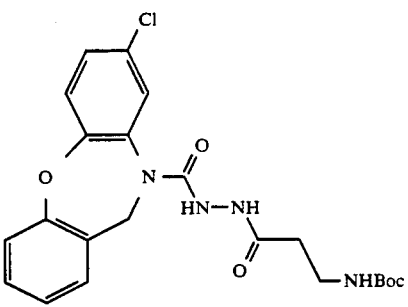

To a stirring solution of 3.78 g (20 mmol) of N-[(1,1-dimethylethoxy)carbonyl]-β-alanine (6), prepared as described above in Example 6, and 5.79 (20 mmol) of 8-chlorodibenz[b,f][1,4]oxazepine-10(11H)carboxylic acid, hydrazine (1), prepared as described above in Example 1, in 50 mL of DMF cooled in an icebath was added 3.5 mL (20 mmol) of DIEA followed by 4.22 g (22 mmol) of N,N-dimethylaminopropylethylcarbodiimide hydrochloride. The reaction was allowed to warm to ambient temperature over a period of 16 hours. To the reaction mixture was added 100 mL of EtoAc and 200 mL of M $KHSO_4$. The layers were separated and then the organic layer was washed with 2×100 mL of M $KHSO_4$, 2×100 mL of a saturated $KHCO_3$ solution, and 100 mL of brine. The organic layer was dried over anhydrous $Na_2SO_4$, filtered, and then concentrated in vacuo. The resulting product was purified by column chromatography to yield 4.75 g (52%) of 8-chlorodibenz[b,f][1,4]oxazepine-10(11)-carboxylic acid, 2-[3-[[(1,1-dimethylethoxy)carbonyl]amino]-1-oxopropyl]hydrazide (7). Analysis calculated for $C_{22}H_{25}N_4O_5Cl$ 0.75 $H_2O$ (M.W. 474.43): C, 55.70; H, 5.63; N, 11.81. Found: C, 55.42; H, 5.76; N, 12.11.

EXAMPLE 8

8-chlorodibenz[b,f][1,4]oxazepine-10(11H)-carboxylic acid, 2-[(benzoylamino)acetyl]hydrazide (8)

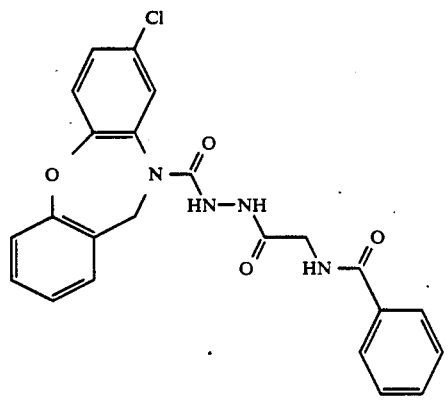

On a two mmol scale, 8-chlorodibenz[b,f][1,4]oxazepine-10(11H)-carboxylic acid, 2-[(benzoylamino)acetyl]hydrazide (8) was prepared from 8- chlorodibenz[b,f][1,4]oxazepine-10(11H)-carboxylic acid, hydrazide (1), prepared as described above in Example 1, and benzoylglycine, in the same manner as described in Example 7 above, to yield 0.36 g (4o%) of product. Analysis calculated for $C_{23}H_{19}N_4O_4Cl$ 0.1 $H_2O$ (M.W. 452.69): c, 61.03; H, 4.28; N, 12.38. Found: C, 60.81; H, 4.25; N, 12.29.

EXAMPLE 9

8-chlorodibenz[b,f][1,4]oxazepine-10(11H)-carboxylic acid, 2-(3-amino-1-oxopropyl]hydrazide. monohydrochloride (9)

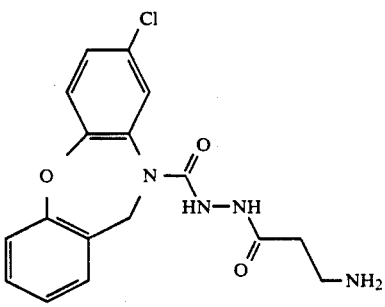

To a solution of 2.30 g (5.0 mmol) of 8-chlorodibenz[b,f]-[1,4]oxazepine-10(11H)-carboxylic acid, 2-[3-[[(1,1-dimethylethoxy)carbonyl]amino]-1-oxopropyl]hydrazide (7), prepared as described above in Example 7, in 8 mL of acetic acid (HOAc) was added 8 mL of 6.8 N HCl/dioxane. After 15 minutes, the solvent was removed under $H_2O$ aspirator vacuum. The resulting residue was triturated with diethyl ether ($Et_2O$). The resulting white solid was collected on a sintered glass funnel and dried in a vacuum oven at 70° C. for 16 hours. A yield of 1.62 g (81%) of 8-chlorodibenz[b,f][1,4]oxazepine-10(11H)-carboxylic acid, 2-(3-amino-1-oxopropyl)hydrazide, monohydrochloride (9) was isolated. Analysis calculated for $C_{17}H_{17}N_4O_3Cl$ 0.9 HCl 1.5 $H_2O$: C, 48.54; H, 5.01; N, 13.32; Cl, 16.01. Found: C, 48.70; H, 4.77; N, 12.87; Cl, 16.07.

EXAMPLE 10

8-chlorodibenz[b,f][1,4]oxazepine-10(11H)-carboxylic acid, 2-[1-oxo-3-[[[[(4-trifluoromethyl)phenyl]amino]carbonyl]-amino]propyl]hydrazide (10)

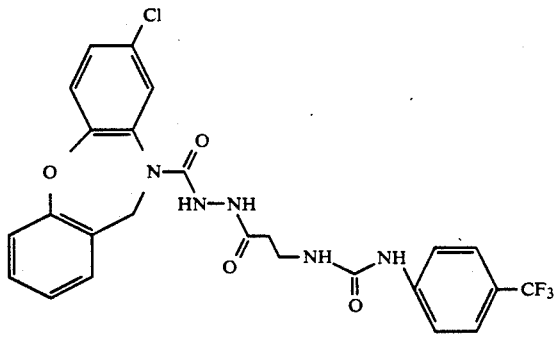

To a stirring solution of 0.40 g (i mmol) of 8-chlorodibenz[b,f][1,4]oxazepine-10(11H)-carboxylic acid, 2-(3-amino-1-oxopropyl)hydrazide, monohydrochloride (9), prepared as described above in Example 9, in 5 mL of pyridine was added 0.22 g (1.2 mmol) of 4-trifluoromethylphenylisocyanate. After 64 hours, the solvent was removed under aspirator vacuum. The resulting residue was dissolved in 10 mL of EtOAc. The organic layer was then washed with 2×10 mL of M $KHSO_4$ and 2×10 mL of $H_2O$. The organic layer was then dried over anhydrous $Na_2SO_4$, filtered, and concentrated in vacuo. The resulting residue was triturated with EtOAc, and then the resulting solid was collected on a sintered glass funnel and dried in a steam cabinet. The yield of 8-chlorodibenz[b,f][1,4]oxazepine-10(11H)-carboxylic acid, 2-[1-oxo-3-[[[[(4-trifluoromethyl)phenyl]amino]carbonyl]-amino]-propyl]hydrazide (10) was 0.17 g (31%). Additional product (0.23 g, 42%) was in the filtrate. Analysis calculated for $C_{25}H_{21}N_5O_4ClF_3$ (M.W. 547.92): C, 54.80; H, 3.86; N, 12.78; Cl, 6.47; F, 10.40. Found: C, 54.62; H, 3.68; N, 12.42; Cl, 6.63; F, 10.82.

EXAMPLE 11

8-chlorodibenz[b,f][1,4]oxazepine-10(11H)-carboxylic acid,

2-[3-[(methylsulfonyl)amino]-i-oxopropyl]hydrazide (11)

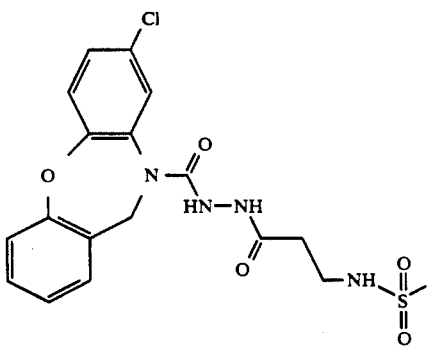

8-chlorodibenz[b,f][1,4]oxazepine-10(11H)-carboxylic acid, 2-[-3-[(methylsulfonyl)amino]-1-oxopropyl]hydrazide (11) was prepared from 8-chlorodibenz[b,f][1,-4]oxazepine-10(11H)carboxylic acid, 2-(3-amino-1-oxopropyl)hydrazide, monohydrochloride (9), prepared as described above in Example 9, and methanesulfonyl chloride, in the manner described in Example 10 above, on a 2-mmol scale to yield 0.46 g (52%) of product. Analysis calculated for $C_{18}H_{19}N_4O_5ClS$ (M.W. 438.88): C, 49.26; H, 4.36; N, 12.77. Found: C, 49.05; H, 4.40; N, 12.66.

EXAMPLE 12

8-chlorodibenz[b,f][1,4]oxazepine-10(11H)-carboxylic acid, 8-chlorodibenz[b,f][1,4]oxazepine-10(11H)-carboxylic acid, 2-[3[[(methylamino)carbonyl]amino]-1-oxopropyl]hydrazide (12)

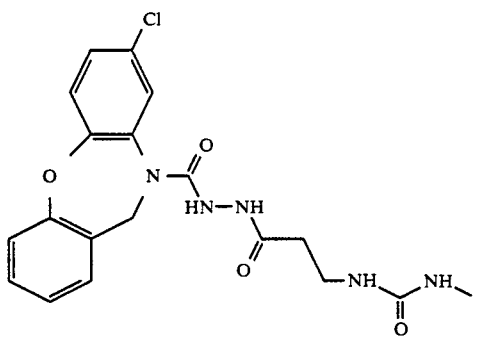

8-chlorodibenz[b,f][1,4]oxazepine-10(11H)-carboxylic acid, 2-[3-[[(methylamino)carbonyl]amino]-1-oxopropyl]hydrazide (12) was prepared from 8-chlorodibenz[b,f][1,4]oxazepine-10(11H)-carboxylic acid, 2-(3-amino-1-oxopropyl)hydrazide, monohydrochloride (9), prepared as described above in Example 9, and methylisocyanate, in the manner described in Example 10 above, on a one mmol scale to yield 0.17 g (40%) of product. Analysis calculated for $C_{19}H_{20}N_5O_4Cl$ 0.4 $H_2O$ (M.W. 425.06): C, 53.69; H, 4.93; N, 16.48; Cl, 8.34. Found: C, 53.96; H, 4.87; N, 16.06; Cl, 8.46.

EXAMPLE 13

N-(methylsulfonyl)-L-phenylalanine, methyl ester (13)

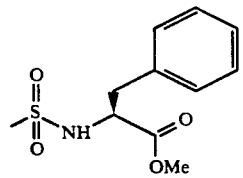

To a stirring solution of 2.51 g (20.0 mmol) of methyl L-phenylalaninate hydrochloride and 6.7 mL (48 mmol) of TEA in 50 mL of DMF was added 1.86 mL (24 mmol) of methanesulfonyl chloride. After 16 hours, the reaction mixture was added to 200 mL of $H_2O$ and 200 mL of EtOAc. The resulting layers were separated, and the organic layer was washed with 3x 200 mL of $H_2O$ and dried. The resulting residue was chromatographed to yield 2.54 g (49%) of N-(methylsulfonyl)-L-phenylalanine, methyl ester (13), which was a clear colorless glass. Analysis calculated for $C_{11}H_{15}NO_4S$ (M.W. 257.30): C, 51.35; H, 5.88; N, 5.44; S, 12.46. Found: C, 50.92; H, 5.92; N, 5.38; S, 12.55.

EXAMPLE 14

N-(methylsulfonyl)-L-phenylalanine, hydrazide (14)

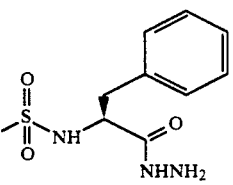

To a stirring solution of 0.51 g (2.0 mmol) of N-(methylsulfonyl)-L-phenylalanine, methyl ester (13), prepared as described above in Example 13, in 2 mL of EtOH was added 0.20 g (4.0 mmol) of hydrazine hydrate. After refluxing for 2 hours, the reaction mixture was stirred for 16 hours at ambient temperature. An additional 0.30 g of hydrazine hydrate was then added to the reaction. After refluxing for 6 hours and stirring at ambient temperature for 16 hours, the reaction solvent was removed under vacuum. The resulting residue was chromatographed to yield 0.25 g (50%) of N-(methylsulfonyl)-L-phenylalanine, hydrazide (14). This product was employed immediately as described below in Example 15.

EXAMPLE 15

8-chlorodibenz[b,f][1,4]oxazepine-10(11H)-carboxylic acid,
2-[(methylsulfonyl)amino]-1-oxo-3-phenyl]hydrazide (15)

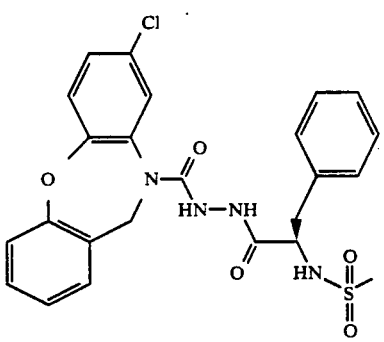

8-chlorodibenz[b,f][1,4]oxazepine-10(11H)-carboxylic acid, 2,[2-((methylsulfonyl)amino]-1-oxo-3-phenyl]hydrazide (15) was prepared in the manner described above in Example 5 on a 0.51 mmol scale starting with N-(methylsulfonyl)-L-phenylalanine, hydrazide (14), prepared as described above in Example 14, and 8-chlorodibenz[b,f][1,4]-oxazepine-10(11H)-carbonyl chloride (2), prepared as described above in Example 2, to yield 0.11 g (42%) of product. Analysis calculated for $C_{24}H_{23}N_4O_5SCl$ (M.W. 514.98): C, 55.98; H, 4.50; N, 10.88; Cl, 6.88. Found: C, 55.81; H, 4.46; N, 10.66; Cl, 6.96.

EXAMPLE 16

Methyl 4-oxohexanoate (16)

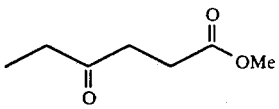

To a stirring suspension of 8.15 g (25 mmol) of $Cs_2CO_3$ in DMF was added 5.79 g (44 mmol) of 4-oxohexanoic acid. After 5 minutes, 6.81 g (48 mmol) of iodomethane was added. The reaction mixture was stirred at ambient temperature for 16 hours. To the reaction was then added 250 mL of EtOAc and 250 mL of $H_2O$. The layers were separated, and the organic layer was washed with $3 \times 250$ mL of $H_2O$. The organic layer was then dried over $Na_2SO_4$ anhydrous, filtered, and concentrated under vacuum. The yield of methyl 4-oxohexanoate (16) was 4.15 g (65%), which was employed in Example 17 below.

EXAMPLE 17

Methyl 2-ethyl-1,3-dioxolane-2-propanoate (17)

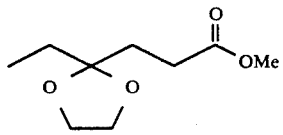

To a stirring solution of 4.05 g (28 mmol) of methyl 4-oxohexanoate (16), prepared as described above in Example 16, in 200 mL of toluene and 0.53 g (2.8 mmol) of tosyl acid was added 5.59 g (90 mmol) of ethylene glycol. After refluxing for 2 hours using a Dean-Stark trap, the solvent was removed under vacuum. The resulting orange oil was dissolved in 200 mL of EtoAc. The EtoAc was then washed with $2 \times 200$ mL of $H_2O$. The organic layer was then dried over Na2S04 anhydrous, filtered, and concentrated in vacuo to yield 4.96 g (94%) of methyl 2-ethyl-1,3-dioxolane-2-propanoate (17), which was employed immediately in Example 18 below.

EXAMPLE 18

8-chlorodibenz[b.f][1,4]oxazepine-10(11H)-carboxylic acid, 2-[3-(2-ethyl-1,3-dioxolan-2-yl)-1-oxopropyl]hydrazide (18 )

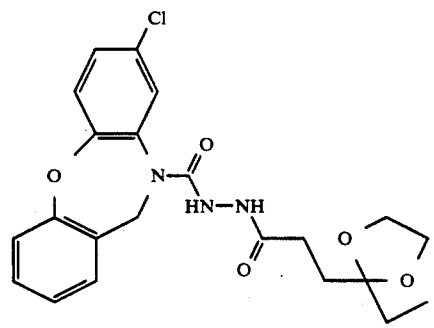

8-chlorodibenz[b,f][1,4]oxazepine-10(11H)-carboxylic acid, 2-[3-(2-ethyl-1,3-dioxolan-2-yl)-1-oxopropyl]-hydrazide (18) was prepared as described in A. Benderly et al., "A New Synthesis of Carboxylic Acid Hydrazides Via Organoaluminum Reagents," *Tetrahedron Lett.*, 29, 739 (1988).

To a stirring suspension of 1.45 g (5.0 mmol) of 8-chlorodibenz[b,f][1,4]oxazepine-10(11H)-carboxylic acid, hydrazide (1), prepared as described above in Example 1, in 10 mL of chloroform, was added 6.24 mL (12.5 mmol) of trimethyl aluminum ($Me_3Al$). After 1 hour of stirring, 0.94 g (5.0 mmol) of methyl 2-ethyl-1,3-dioxolane-2-propanoate (17), prepared as described above in Example 17, was added to the reaction mixture, and the resulting reaction mixture was stirred for 16 hours. To the reaction was then slowly added 50 mL of a saturated solution of $KHCO_3$. The reaction mixture was then extracted with $3 \times 50$ mL of EtOAc. The organic layer was then dried and chromatographed to yield 0.21 g (10%) of product. Analysis calculated for $C_{22}H_{24}N_3O_5$ Cl (M.W. 445.93): C, 59.25; H, 5.44; N, 9.43; Cl, 7.95. Found: C, 59.13; H, 5.59; N, 9.27; Cl, 8.18.

EXAMPLE 19

8-chlorodibenz[b,f][1,4]oxazepine-10(11H)-carboxylic acid, 2-(bromoacetyl) hydrazide (19)

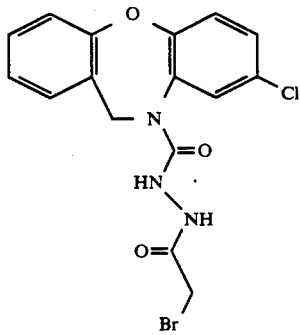

To an icebath-cooled stirring solution of 5.79 g (20 mmol) of 8-chlorodibenz[b,f][1,4]oxazepine-10(11H)-carboxylic acid, hydrazide (1), prepared as described above in Example 1, 3.1 mL (22 mmol) of TEA, and 0.16 g (1 mmol) of dimethylaminopyridine in 50 mL of DMF was added 4.44 g (22 mmol) of bromoacetyl bromide. After 16 hours of stirring, the reaction mixture was added to 250 mL of brine and 250 mL of EtOAc. The resulting layers were separated, and the organic layer was washed with $4 \times 250$ mL of brine. The organic layer was then dried and chromatographed. The yield of 8-chlorodibenz[b,f][1,4]oxazepine-10(11H)-carboxylic acid, 2-(bromoacetyl) hydrazide (19) was 3.75 g (45%). The product was employed immediately in the manner described in Example 20 below.

EXAMPLE 20

8-chlorodibenz[b,f][1,4]oxazepine-10(11H)-carboxylic acid, 2-(diethoxyphosohinyl)acetyl]hydrazide (20)

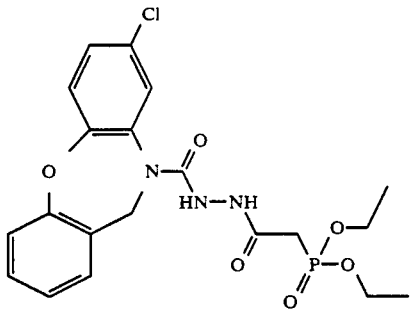

To a stirring solution of 2.57 g (6.3 mmol) of 8-chlorodibenz[b,f][1,4]oxazepine-10(11H)-carboxylic acid, 2bromoacetyl) hydrazide (19), prepared as described in Example 19 above, in 75 mL of tetrahydrofuran (THF) was added 1.25 g (7.5 mmol) of triethylphosphite and 0.15 g (1 mmol) of NaI. After 22 hours of refluxing, an additional 0.62 g (3.75 mmol) of triethylphosphite and 0.05 g (0.33 mmol) of NaI were added to the reaction, which was refluxed an additional 24 hours. The solvent was then removed under aspirator vacuum, and the reaction mixture was chromatographed to yield 2.46 g (83%) of 8-chlorodibenz-[b,f][1,4]oxazepine-10(11H)-carboxylic acid, 2-[(diethoxyphosphinyl-)acetyl]hydrazide (20), which was a beige foam. Analysis calculated for $C_{20}H_{23}N_{23}O_6PCl$ (M.W. 467.85): C, 51.35; H, 4.96; N, 8.98; Cl, 7.58. Found: C, 51.02; H, 5.03; N, 8.83; Cl, 7.39.

EXAMPLE 21

N-(ethylsulfonyl)-β-alanine, methyl ester (21)

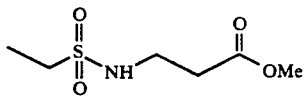

N-(ethylsulfonyl)-β-alanine, methyl ester (21) was prepared from methyl β-alaninate and ethanesulfonyl chloride on a 32 mmol scale in the manner described in Example 13 above to yield 1.53 g (24%) of product. Analysis calculated for $C_6H_{13}NO_4S$ 0.25 $H_2O$ (M.W. 199.74): C, 36.08; H, 6.81; N, 7.01; S, 16.05. Found: C, 36.03; H, 6.82; N, 6.97; S, 15.59.

EXAMPLE 22

8-clhorodibenz[b,f1[1,4]oxazepine-10(11H)-carboxylic acid, 2-3-(ethylsulfonyl)amino1-1-oxopropyl]hydrazide (22)

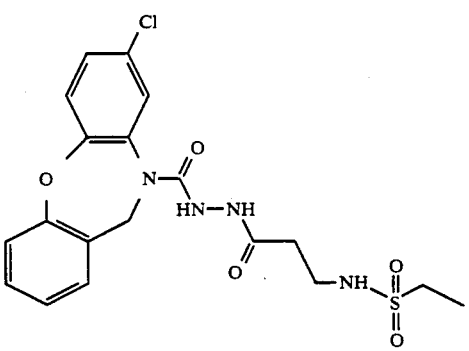

8-chlorodibenz[b,f][1,4]oxazepine-10(11H)-carboxylic acid, 2-[3-[(ethylsulfonyl)amino]-1-oxopropyl]hydrazide (22) was prepared from N-(ethylsulfonyl)-β-alanine, methyl ester (21), prepared as described above in Example 21, and 8-chlorodibenz[-b,f][1,4]-oxazepine-10(11H)-carboxylic acid, hydrazide (1), prepared as described above in Example 1, in the manner described in Example 18 above on a 2.0 mmol scale to yield 0.25 g (28%) of product. Analysis calculated for $C_{19}H_{21}NO_5SCl$ 0.75 $H_2O$ (M.W. 466.43): C, 48.93; H, 4.86; N, 12.01; Cl, 7.60; S, 6.87. Found: C, 49.05; H, 4.61; N, 11.78; Cl, 8.34; S, 6.69.

EXAMPLE 23

N-(phenylsulfonyl)-8-alanine, methyl ester (23)

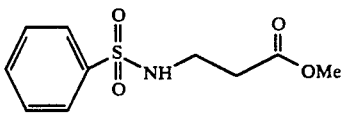

N-(phenylsulfonyl)-β-alanine methyl ester (23) was prepared from methyl β-alaninate and phenylsulfonyl chloride on a 32 mmol scale in the manner described above in Example 13 to yield 6.76 g (86%) of product. Analysis calculated for $C_{10}H_{13}NO_4S$ (M.W. 243.28): C, 49.37; H, 5.39; N, 5.76; S, 13.18. Found: C, 49.06; H, 5.46; N, 5.78; S, 12.95.

EXAMPLE 24

8-chlorodibenz[b,f1[1,4]oxazepine-10(11H)-carboxylic acid, 2-[1-oxo-3-[(phenylsulfonyl)amino]propyl]hydrazide (24)

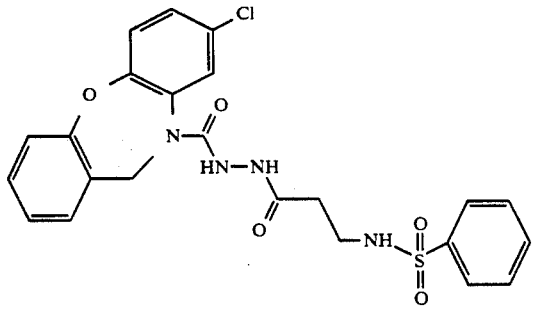

8-chlorodibenz[b,f][1,4]oxazepine-10(11H)-carboxylic acid, 2-[3-[(phenylsulfonyl)amino]-1-oxopropyl]hydrazide (24) was prepared from N-(phenylsulfonyl)-β-alanine, methyl ester (23), prepared as described above in Example 23, and 8-chlorodibenz[b,f][1,4]-oxazepine-10(11H)-carboxylic acid, hydrazide (1), prepared as described above in Example 1, on a two mmol scale in the manner described in Example 18 above to yield 0.44 g (44%) of product.

EXAMPLE 25

Methyl 2-methyl-1,3-dioxolane-2-butanoate (25)

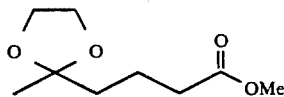

Methyl 2-methyl-I,3-dioxolane-2-butanoate (25) was prepared from methyl 5-oxohexanoate and ethylene glycol in the manner described in Example 17 above on a 28 mmol scale to yield 4.94 g (94%) of product. The product was employed immediately in the manner described in Example 26 below.

EXAMPLE 26

8-chlorodibenz[b,f][1,4]oxazepine-10(11H)-carboxylic acid, 2-[4-(2-methyl-1,3-dioxolan-2-yl)-1-oxobutyl]hydrazide (26)

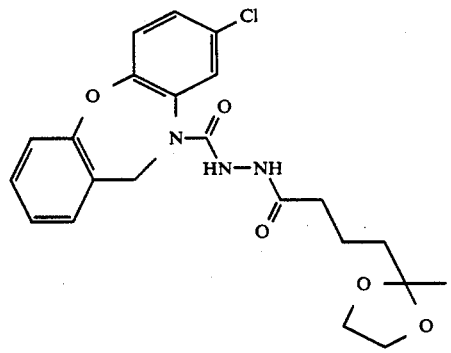

8-chlorodibenz[b,f][1,4]oxazepine-10(11H)-carboxylic acid, 2-[4-(2-methyl-1,3-dioxolan-2-yl)-1-oxobutyl]-hydrazide (26) was prepared in the manner described above in Example 18 from methyl 2-methyl-1,3-dioxolane-2-butanoate (25), prepared as described above in Example 25, and 8-chlorodibenz[b,f][1,4]oxazepine-10(11H)-carboxylic acid, hydrazide (1), prepared in the manner described above in Example 1, on a 2 mmol scale to yield 0.47 g (53%) of product. Analysis calculated for $C_{22}H_{24}N_3O_5Cl$ 0.2 $H_2O$ (M.W. 449.51): C, 58.79; H, 5.74; N, 9.35; Cl, 9.15. Found: C, 58.47; H, 5.58; N, 9.30; Cl, 9.15.

EXAMPLE 27

8-chlorodibenz[b,f1[1,4]oxazeopine-10(11H)-carboxylic acid, 2-[(ethoxyhydroxyphosphinyl)acetyl]hydrazide (27)

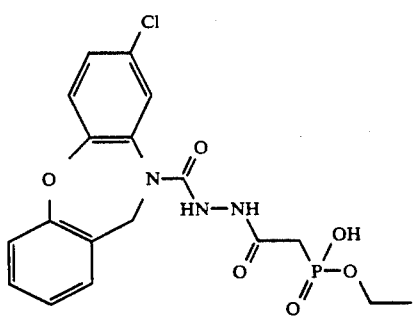

To a stirring solution of 0.58 g (1.2 mmol) of 8-chlorodibenz[b,f][1,4]oxazepine-10(11H)-carboxylic acid, 2-[(diethoxyphosphinyl)acetyl]hydrazide (20), prepared as described in Example 20, in 5 mL of THF:methanol (THF:MeOH) (3:2) was added 2 mL of N NaoH. After 24 hours of stirring, an additional 2 mL of NaoH was added to the reaction. After 7 days of stirring, the reaction mixture was filtered, and the resulting filtrate was extracted with 25 mL of EtOAc. The aqueous layer was neutralized with N HOl to pH 2, and was extracted with 25 mL of dichloromethane (DCM). The organic layer was dried over $Na_2SO_4$ anhydrous, filtered, and then concentrated in vacuo. The yield of 8-chlorodibenz[b,f][1,4]oxazepine-10(11H)-carboxylic acid, 2-[(ethoxyhydroxyphosphinyl)acetyl]hydrazide (27), which was a beige foam, was 0.20 g (37%). Analysis calculated for $C_{18}H_{19}N_3O_6pCl$ 025 $H_2O$ (M.W. 443.30): C, 48.66; H, 4.42; N, 9.46. Found: C, 48.62; H, 4.37; N, 9.24.

EXAMPLE 28

8-chlorodibenz[b,f][1,4]oxazeopine-10(11H)-carboxylic acid, 2-(phosphonoacetyl)hydrazide (28)

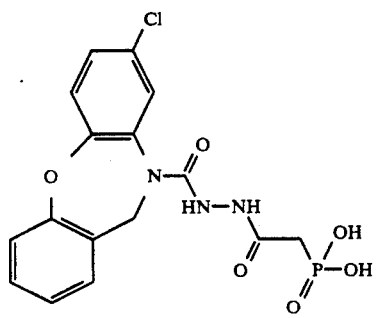

To a stirring solution of 0.21 g (0.45 mmol) of 8-chlorodibenz[b,f][1,4]oxazepine-10(11H)-carboxylic acid, 2-[(diethoxyphosphinyl)acetyl]hydrazide (20), prepared as described above in Example 20, in 5 mL of CH$_3$CN. Was added 0.134 g (0.9 mmol) of NaI and 0.136 g (0.9 mmol) of trimethylsilyl chloride. The reaction was stirred for three days at room temperature, followed by 14 hours of refluxing. After removing the solvent by vacuum, the product was isolated by reverse chromatography on a Supelco C-18 column in 50% H$_2$O:50% CH$_3$CN:1% acetic acid. The yield of 8-chlorodibenz[b,f][1,4]oxazepine-10(11H)-carboxylic acid, 2-(phosphonoacetyl)hydrazide (28) was 0.081 g (45%). Analysis calculated for C$_{16}$H$_{15}$N$_3$O$_6$PCl.1.25 H$_2$O (M.W. 434.26): C, 44.25; H, 4.06, N, 9.68. Found: C, 43.95; H, 3.80; N, 9.56.

EXAMPLE 29

8-chlorodibenz[b,f][1,4]oxazeopine-10(11H)-carboxylic acid,
2-[3-[[(1-methyl-2-pyrrolyl)carbonyl]amino]-1-oxo-propyl]hydrazide(29)

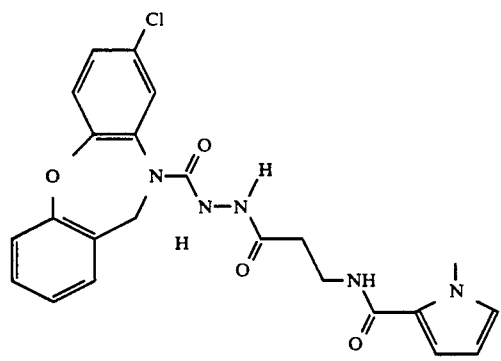

8-chlorodibenz[b,f][1,4]oxazepine-10(11H)-carboxylic acid, 2-[3-[[(1-methyl-2-pyrrolyl)carbonyl]amino]-1-oxopropyl]hydrazide (29) was prepared from 8-chlorodibenz[b,f][1,4]oxazepine-10(11H)-carboxylic acid, 2-(3-amino-1-oxopropyl) hydrazide, monohydrochloride (9), prepared as described above in Example 9, and 1-methylpyrrole-2-carbonyl chloride in the same manner as described in Example 10 on a 1.9 mmol scale to yield 0.58 g (66%) of product. Analysis calculated for C$_{23}$H$_{22}$N$_5$O$_4$Cl (M.W. 467.92): C, 59.04; H, 4.74; N, 14.95; Cl, 7.58. Found: C, 59.22; H, 4.73; N, 14.95; Cl, 7.75.

EXAMPLE 30

8-chlorodibenz[b,f][1,4]oxazepine-10(11H)-carboxylic acid
2-[1-oxo-3-[(2-thienylsulfonyl)amino1propyl]hydrazide (30)

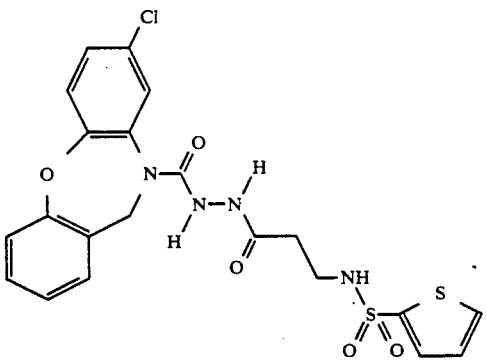

8-chlorodibenz[b,f][1,4]oxazepine-10(11H)-carboxylic acid, 2-[1-oxo-3-[(2-thienylsulfonyl)amino]propyl hydrazide (30) was prepared from 8-chlorodibenz[b,f][1,4]oxazepine-10(11H)carboxylic acid, 2-(3-amino-1-oxopropyl)hydrazide, monohydrochloride (9), prepared as described above in Example 9, and 2-thiophenesulfonyl chloride in the same manner as described in Example 10 on a 1.9 mmol scale to yield 0.48 g (50%) of product. Analysis calculated for C$_{21}$H$_{19}$N$_4$O$_5$ClS$_2$ (M.W. 506.99): C, 49.26; H, 4.36; N, 12.77; Cl, 6.99; S, 12.65. Found: C, 49.05; H, 4.40: N, 12.66; Cl, 7.13; S, 12.88.

EXAMPLE 31

8-chlorodibenz[b,f][1,4]oxazeopine-10(11H)-carboxylic acid.
2-[3-(2-furanylcarbonyl)amino]-1-oxopropyl]hydrazide (31)

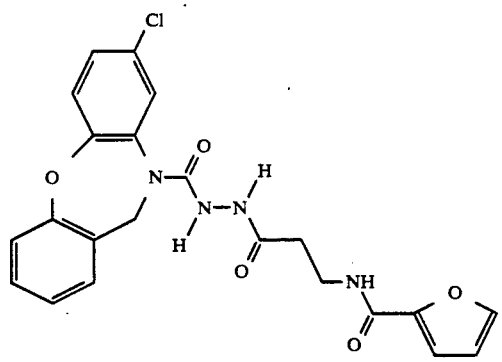

8-chlorodibenz[b,f][1,4]oxazepine-10(11H)-carboxylic acid, 2-[3-[(2-furanylcarbonyl)amino]-1-oxopropyl]hydrazide (31) was prepared from 8-chlorodibenz[b,f][1,4]oxazepine-10(11H)-carboxylic acid, 2-(3-amino-1-oxopropyl)hydrazide, monohydrochloride (9), prepared in the manner described above in Example 9, and 2-furoyl chloride in the same manner as described in Example 10 on a 1.9 mmol scale to yield 0.37 g (43%) of product Analysis calculated for C$_{22}$H$_{19}$N$_4$O$_5$Cl (M.W. 454.87): C, 49.26; H, 4.36; N, 12.77; Cl, 7.79. Found: C, 49.05; H, 4.40; N, 12.66; Cl, 7.58.

EXAMPLE 32

4-chloro-2-nitro-1-(phenylthio)benzene (32)

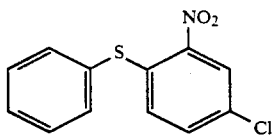

To a stirring solution of 10.0 g (91 mmol) of thiophenol in 170 mL of DMF is added 6.2 g (95 mmol) of KOH. When the KOH has dissolved, i7 g (91 mmol) of 2,5-dichloronitrobenzene is added. After stirring for 3 hours at 70° C., the solvent is removed in vacuo. The residue is partitioned between CHCl$_3$ and N NaOH. The organic layer is washed with N NaOH, H$_2$O, N HCl, H$_2$O and is dried over NaSO$_4$ anhydrous, filtered, and stripped. The product is crystallized from cyclohexane.

EXAMPLE 33

5-chloro-2-(phenylthio]benzeneamine (33)

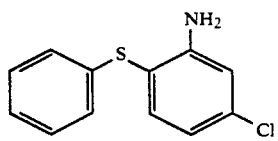

An ethanol solution of 1.0 g (4.2 mmol) of 4-chloro-2-nitro-1-(phenylthio)benzene (32), prepared in the manner described above in Example 32, is shaken in a Parr hydrogenator at 30 psi hydrogen with Raney nickel at room temperature for 3 hours. The catalyst is filtered from the reaction, and the solution is concentrated under vacuum.

EXAMPLE 34

8-chlorodibenzo[b,f][1,4]thiazeoin-11(10H)-one (34)

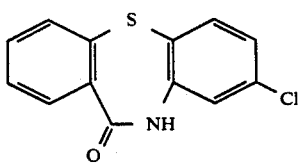

To a stirring 1.93 M solution of phosgene in 5.5 mL of toluene cooled in an icebath is added dropwise 0.5 g (2.1 mmol) of 5-chloro-2-(phenylthio)benzeneamine (33), prepared in the manner described above in Example 33, in 8 mL of toluene. After stirring for 30 minutes at 5° C., the reaction mixture is heated on a steam bath for 30 minutes. The solvent is removed under vacuum.

The residue is taken up in 2.5 mL of bromobenzene and is added dropwise to 0.29 g (2.2 mmol) of AlCl3 in 2.5 mL of bromobenzene. The stirring reaction mixture is heated at 100° C. for 1 hour. The reaction mixture is poured over H$_2$O. The resulting solid is collected and is washed with CHCl$_3$ and Et$_2$O.

EXAMPLE 35

8-chloro-10,11-dihydrodibenzo[b,f][1,4]thiazepine (35)

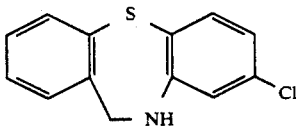

To a stirring solution of 5.23 g (20 mmol) of 8-chlorodibenzo[b,f][1,4]thiazepin-11(10H)-one (34), prepared in the manner described above in Example 34, in 175 mL of THF cooled in an ice bath is added dropwise 100 mL of M lithium aluminum hydride solution. The reaction is heated at reflux for 4 hours. The reaction is quenched by the addition of 3.8 mL of 15% NaOH and 15.2 mL of H$_2$O. The reaction mixture is filtered through a pad of celite. The filtrate is concentrated in vacuo and is recrystallized from cyclohexane.

EXAMPLE 36

8-chlorodibenzo[b,f][1,4]thiazepine-10(11H)-carbonyl chloride (36)

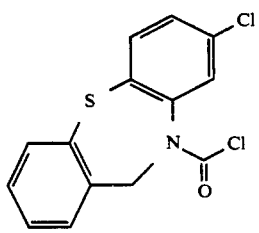

8-chlorodibenzo[b,f][1,4]thiazepine-10(11H)-carbonyl chloride (36) is prepared in the manner described in Example 2 using 8-chloro-10,11-dihydrodibenzo[b,f][1,4]thiazepine (35), prepared in the manner described above in Example 35.

EXAMPLE 37

8-chlorodibenzo[b,f][1,4]thiazepine-10(11H)-carboxylic acid, 2-1-oxo-3-[(2-thienylacetyl)amino1propyl]hydrazide (37)

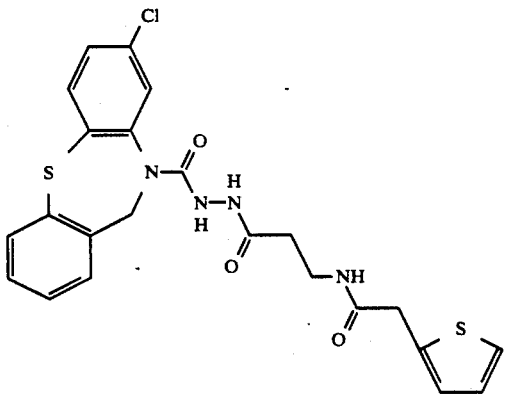

8-chlorodibenzo[b,f][1,4]thiazepine-10(11H)-carboxylic acid, 2-[1-oxo-3-[(2-thienylacetyl)amino]propyl]hydrazide (37) is prepared from 8-chlorodibenzo[b,f][1,4]thiazepine-10(11H)-carbonyl chloride (36), prepared in the manner described above in Example 36, and N-(2-thienylacetyl)-β-alanine, hydrazide (4), prepared in the manner described above in Example 4, in the same manner as described in Example 5.

EXAMPLE 38

8-chloro-5-oxodibenzo[b,f][1,4]thiazepine-10(11H)-carboxylic acid,
2-[1-oxo-3-[(2-thienylacetyl)amino]propyl]hydrazide (38)

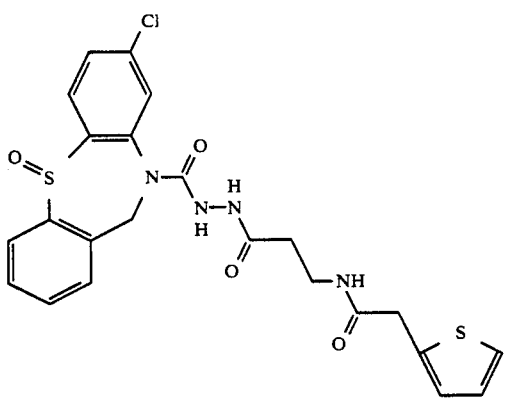

To a stirring solution of 0.7 g (1.5 mmol) of 8-chlorodibenzo[b,f][1,4]thiazepine-10(11H)-carboxylic acid, 2-[1-oxo-3-[(2-thienylacetyl)amino]propyl]hydrazide (37), prepared in the manner described above in Example 37, in 5 mL of HOAc is added 0.13 mL (1.5 mmol) of 30% H$_2$O$_2$. After stirring for 1 hour, the reaction mixture is lyophilized to obtain the product.

EXAMPLE 39

8-chlorodibenzo[b,f][1,4]thiazepine-10(11H)-carboxylic acid,
2-[1-oxo-3-[(2-thienylacetyl)amino]propyl]-hydrazide,5,5-dioxide (39)

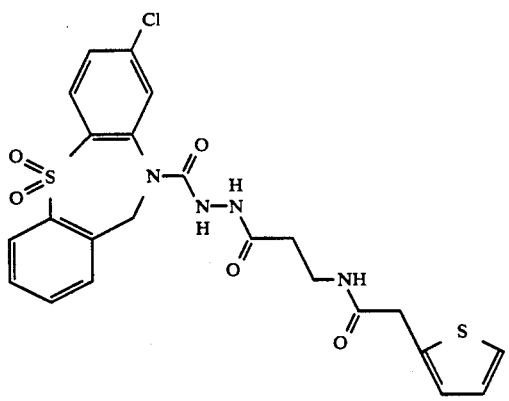

To a stirring solution of 0.7 g (1.5 mmol) of 8-chloro-5oxodibenzo[b,f][1,4]thiazepine-10(11H)-carboxylic acid, 2-[1-oxo-3-[(2-thienylacetyl)amino]propyl]hydrazide (38), prepared in the manner described above in Example 38, in 5 mL of HOAc is added 0.13 mL (1.5 mmol) of 30% H$_2$O$_2$. The reaction mixture is heated for 16 hours at 60° C. The reaction mixture is lyophilized to obtain the product.

EXAMPLE 40

8-(trifluoromethyl)dibenz[b,f][1,4]oxazepine-10(11H)-carbonyl chloride (40)

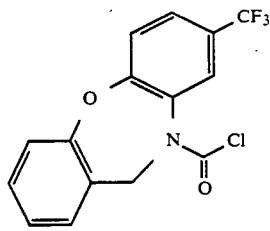

8-(trifluoromethyl)dibenz[b,f][1,4]oxazepine-10(11H)-carbonyl chloride (40) is prepared in the manner described in U.S. Pat. No. 3,534,019.

200 parts of 4-chloro-3-nitrobenzotrifluoride is heated to 160° C. and stirred and 160 parts of the potassium salt of salicylaldehyde is added over a period of 30 minutes. After the addition is complete, an exothermic reaction takes place and the temperature rises to about 195° C. Heating is then discontinued until the reaction subsides and the mixture is then heated for 1 hour at 150° C. The mixture is cooled, ice and water are added, and it is then extracted With ether. The ether layer is filtered to remove insoluble material and the resultant solution is dried over sodium sulfate. The ether solvent is then evaporated and the residual oil is recrystallized from a mixture of hexane and benzene to give 2-(2-nitro-4-trifluoromethyl-phenoxy)benzaldehyde melting at about 79°-81° C.

A solution of 55 parts of the ether obtained in the preceding paragraph in 800 parts of ethanol is hydrogenated over Raney nickel catalyst at room temperature and atmospheric pressure. When hydrogen uptake ceases, the catalyst is removed by filtration and the ethanol solvent is evaporated. The residue is then dissolved in 500 parts by volume of hexane, filtered, and then cooled. There is then obtained yellowish-white crystals which are separated by filtration to give 8-(trifluoromethyl)-dibenz-[b,f][1,4]oxazepine-10(11H) melting at about 86°-88° C.

13 parts of phosgene in 45 parts of toluene is stirred at 5°-10° C. and 70 parts of ether is added. This is followed by the addition of a solution of 18.9 parts of 8-(trifluoromethyl)-dibenz-[b,f][1,4]oxazepine-10(11H) and 7.2 parts of triethylamine in 140 parts of ether. After the addition is complete, the mixture is stirred for 2 hours and then filtered and the solvent is evaporated from the filtrate. The residue is dissolved in 200 parts by volume of hot hexane and this mixture is then filtered and cooled. This gives 8-(trifluoromethyl)dibenz[b,f][1,4]-oxazepine-10(11H)-carbonyl chloride (40), melting at about 102°-105° C.

EXAMPLE 41

8-(trifluoromethyl)dibenz[b,f1(1,4)oxazepine-10(11H)-carboxylic acid,
2-[1-oxo-3-[(2-thienylacetyl)amino]propyl]hydrazide (41)

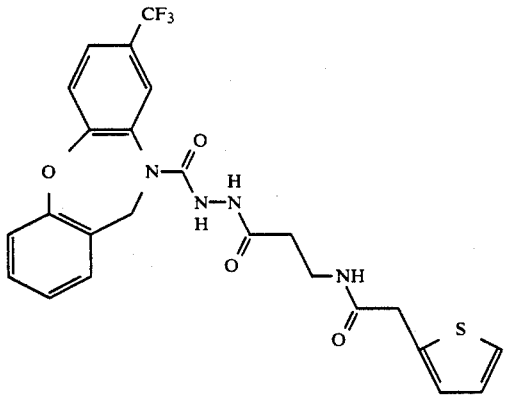

8-(trifluoromethyl)dibenz[b,f][1,4]oxazepine-10(11H)carboxylic acid, 2-[1-oxo-3-[(2-thienylacetyl)amino]propyl]hydrazide (41) is prepared from 8-(trifluoromethyl)dibenz-[b,f][1,4]oxazepine-10(11H)-carbonyl chloride (40), prepared in the manner described above in Example 40, and N-(2-thienyl-acetyl)-β-alanine, hydrazide (4), prepared in the manner described above in Example 4, in the same manner as described in Example 5.

EXAMPLE 42

2-chloro-10, 11-dihydrodibenz[b.f1[1,4]-oxazepine (42)

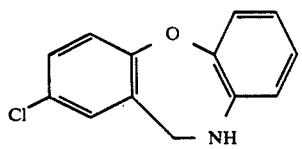

2-chloro-10,11-dihydrodibenz[b,f][1,4]-oxazepine (42) is prepared in the manner described in Example 40, using 2-chloronitrobenzene and 5-chlorosalicylaldehyde.

EXAMPLE 43

2-chlorodibenz[b,f][1,4]oxazepine-10(11H)-carbonyl chloride (43)

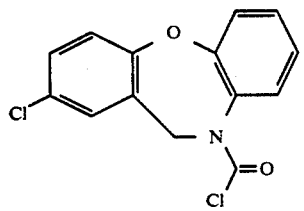

2-chlorodibenz[b,f][1,4]oxazepine-10(11H)-carbonyl chloride (43) is prepared in the manner described in Example 2 using phosgene and 2-chloro-10,11-dihydrodibenz[b,f][1,4]-oxazepine (42), prepared in the manner described above in Example 42.

EXAMPLE 44

2-chlorodibenz[b,f][1,4]oxazepine-10(11H)-carboxylic acid,
2-[1-oxo-3-[(2-thienylacetyl)amino]propyl]hydrazide (44)

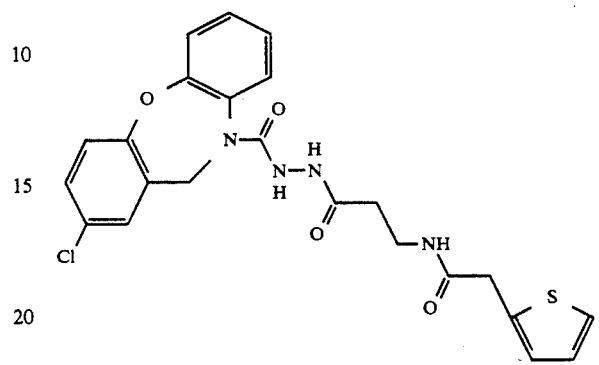

2-chlorodibenz[b,f][1,4]oxazepine-10(11H)-carboxylic acid, 2-[1-oxo-3-[(2-thienylacetyl)amino]propyl]hydrazide (44) is prepared from 2-chlorodibenz[b,f][1,-4]oxazepine-10(11H)-carbonyl chloride (43), prepared as described above in Example 43, and N-(2-thienylacetyl)-β-alanine, hydrazide (4), prepared in the manner described above in Example 4, in the manner described in Example 5.

The foregoing examples are provided to enable one of ordinary skill in the art to practice the present invention. These examples are merely illustrative, however, and should not be read as limiting the scope of the invention as it is claimed in the appended claims.

(7) Description of Assays (a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., Arch. int. Pharmacodyn, 267, 131-140 (1984); C. Vander Wende et al., Fed. Proc., 15, 494 (1956); Koster et al., Fed. proc., 18, 412 (1959); and Witken et al., J. Pharmacol. exp. Ther., 133, 400-408 (1961).]Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I below.

Charles River male albino mice, weighing 20 to 30 grams were used in this assay.

Thirty minutes after subcutaneous or intragastric administration to ten mice of either 10 mg or 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 10 or 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, are presented in Table I below.

The standard initial screening doses of a test compound employed in this assay were 10 and/or 30 mpk per gram of body weight for both routes of administration. If these initial screening doses of the test compound produced analgesia in seven of ten mice, then the effect of additional doses of the test compound on the writhing response was evaluated, and then the $ED_{50}$ dose was generally calculated. (The slopes of the dose-response curves for all test compounds analyzed were compared as described by Tallarida and Murray, *Manual of Pharmacologic Calculations*, Page 11 (Springer Verlag, New York, 1981)).

All $ED_{50}$ doses calculated are also presented in Table I. As Table I shows, the rank order of potency of the more potent compounds of the present invention tested in the Writhing Assay was (referring to the particular example which describes the preparation of the compound): Example 20 > Example 27 > Example 12 > Example 11 > Example 28. Thus, 8-chlorodibenz-b,f][1,4]oxazepine-10(11H)-carboxylic acid, 2-[(diethoxyphosphinyl)acetyl]hydrazide (Example 20) was determined to be the most potent compound of the invention tested and, thus, is the most preferred compound of the present invention.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation.

The ileums were then quickly removed from the guinea pigs and placed in a modified Tyrode solution, a solution which is known to those of skill in the art, containing one-half the usual amount of magnesium ions.

Segments of ileum about 2 cm long were then cut and mounted in a 10-mL tissue bath containing the modified Tyrode solution. The solution was maintained at 37° C. and aerated With a gaseous mixture of 95% oxygen and 5% carbon dioxide.

Submaximal contractions of the ileum segments were then generated by injecting prostaglandin $E_2$ into the bath, and detected isotonically. Data for a control prostagland in $E_2$ dose response curve plotting concentration of prostaglandin $E_2$ versus number of contractions generated was then obtained by experimentally adjusting the dose of the prostaglandin $E_2$ being injected into the tissue bath, in a manner known by those of skill in the art.

Solutions or suspensions containing an initial amount of a test compound in modified Tyrode solution ("test solutions/suspensions") were then separately substituted for the tissue bath. Each test solution/suspension was then kept in constant contact with the ileum tissue, except for brief periods to drain the bath in preparation for rinsing with fresh test solution/suspension. Different doses of prostaglandin $E_2$ were again injected into the test solutions/suspensions. A second prostaglandin $E_2$ dose response curve was then generated for $PGE_2$ in the presence of a test compound.

A dose ratio of $EC_{50}$ doses (that dose of a compound or drug which is necessary to elicit a 50% maximal biological response and, thus, which is necessary to elicit a 50% reduction in the contractions of the guinea pig ileum segments in this assay) was then calculated from the results of each test in a manner known by those of skill in the art. A concentration of test compound was determined to be "active" if it produced a dose ratio significantly greater than that obtained in a series of blank treatments. Duplicate tests were conducted on each concentration of test compound.

If the initial concentration of a test compound was determined to be "active," then varying concentrations of the test compound were then assayed. As is shown in Table 1 below, all test compounds analyzed in this assay were determined to be "active" as prostaglandin $E_2$ antagonists at the initial concentration.

The $pA_2$ value (a statistical constant which is a common measure of expressing the potency of a particular drug as a competitive antagonist) was then calculated for each test compound by schild plot calculations, as described by H. O. Schild, "pA, A New Scale for the Measurement of Drug Antagonism," *Br. J. Pharmacol*, 2, 189 (1947), according to the following mathematical formula:

$$pA_2 = -\log[\text{Test Compound}]$$

to quantitate the effectiveness of the test compounds as prostaglandin $E_2$ antagonists. The higher the value calculated for $pA_2$, the more potent a particular compound is as a prostaglandin $E_2$ antagonist.

The results of this prostaglandin antagonism assay are also presented in Table I below. The compounds of the present invention which were tested in this assay, and for which results are presented in Table I, correspond to the particular examples specified in Table I.

The results in Table I show that all of the compounds of the present invention tested in this assay exhibit activity as prostaglandin $E_2$ antagonists. Some of these compounds, such as 8-chlorobenz-[b,f][1,4]-oxazepine-10(11H)-carboxylic acid, 2-[1-oxo-3-[1-oxo-2-(2-thienyl)-ethylamino]propyl]hydrazide (Example 5), were surprisingly and unexpectedly found to be more than three to four times more effective as prostaglandin E₂ antagonists than prostaglandin E₂ antagonists reported in the literature.

ent invention as described and claimed herein, and that the invention be limited only by the scope of the claims which follow, and that such claims be interpreted as broadly as is reasonable.

TABLE I
Data Generated from the Assays

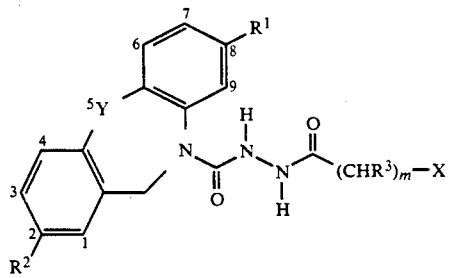

Y = oxygen, sulfur, —SO— or —SO₂—
R¹ = hydrogen, halogen or —CF₃
R² = hydrogen, halogen, —OH or —OCH₃;

| —(CHR³)ₘ—X | Example Number | PBQ WRITHING ASSAY (ED₅₀ (mpk)) I.G. | S.C. | PGE ANTAGONISM IN GUINEA PIG ILEUM (pA₂) |
|---|---|---|---|---|
| | | 10 mpk screening dose | | |
| -2-(CH₂)₂NHCOCH₂-2-thienyl | 5 | **** | Active | Active (7.1) |
| —(CH₂)₂NHBoc* | 7 | Active | Active | Active (5.6) |
| —(CH₂)NHCOPh** | 8 | Active | Active | Not Yet Tested |
| —(CH₂)₂NHSO₂CH₃ | 11 | Active (9.7) | Active (3.0) | Active (6.1) |
| —(CH₂)₂NHCONHCH₃ | 12 | Active (8.4) | **** | Not Yet Tested |
| —CH(Bzl)NHSO₂CH₃*** | 15 | **** | **** | Not Yet Tested |
| | | 30 mpk screening dose | | |
| —(CH₂)₂NHCONH-p-CF₃Ph** | 10 | **** | **** | Active (7.0) |
| —(CH₂)₂C(OCH₂CH₂O)CH₂—CH₃ | 18 | Active | Active | Not Yet Tested |
| —CH₂PO(OCH₂CH₃)₂ | 20 | Active (8.2) | Active (7.1) | Active (6.1) |
| —(CH₂)₂NHSO₂CH₂CH₃ | 22 | **** | **** | Not Yet Tested |
| —(CH₂)₂NHSO₂Ph** | 24 | **** | **** | Active (5.7) |
| —CH₂P(O)(OH)(OCH₂CH₃) | 27 | Active (8.3) | **** | Not Yet Tested |
| —CH₂P(O)(OH)₂ | 28 | Active (11.2) | **** | Not Yet Tested |
| —(CH₂)₂NHCO-2-pyrrolyl-1-N—CH₃ | 29 | Active | **** | Not Yet Tested |
| —(CH₂)₂NHSO₂-2-thienyl | 30 | **** | **** | Not Yet Tested |
| —(CH₂)₂NHCO-2-furanyl | 31 | Active | **** | Not Yet Tested |

*Boc = t-butyloxycarbony
**Ph = phenyl
***Bzl = benzyl
**** = Indicates that, in accordance with the particular conditions set forth above for the Writhing Assay, and under the test criteria employed for that assay, after the administration of an initial screening dosage of 10 or 30 mg per kilogram of the compound, the number of writhes elicited by a mouse injected with PBQ was not equal to, or less than, one-half the median number of writhes recorded for the saline-treated control group of mice that day.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the pres-

What is claimed is:
1. A compound having the formula:

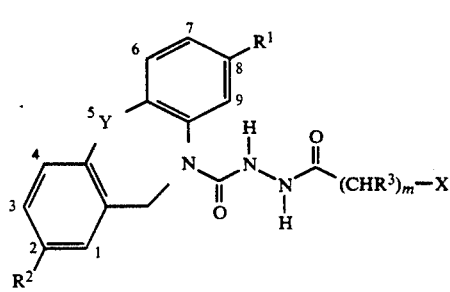

or a pharmaceutically-acceptable salt thereof, wherein:
Y is oxygen, sulfur,

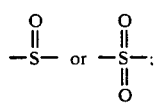

R¹ is hydrogen, halogen or —CF₃;
R² is hydrogen, halogen, —OH or —OCH₃;
R³ is hydrogen, alkyl, aryl, alkyl-substituted aryl or aryl-substituted alkyl;
m is an integer of from 1 to 5;
X is

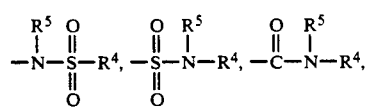

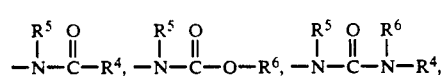

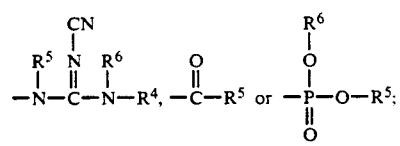

R⁴ is hydrogen, alkyl, aryl, alkyl-substituted aryl, trifluoromethyl-substituted aryl or aryl-substituted alkyl; and R⁵ and R⁶ are each independently hydrogen, alkyl, aryl, alkyl-substituted aryl or aryl-substituted alkyl wherein the term "aryl" used throughout the claim is defined to mean any of the following groups: phenyl, thienyl, furanyl, pyridinyl, imidazolyl, pyrimidyl, (is)oxazolyl, thiazolyl, triazolyl, tetrazolyl or pyrrolyl.

2. A compound of claim 1 wherein R¹ is halogen.
3. A compound of claim 2 wherein R² is hydrogen.
4. A compound of claim 3 wherein
X is

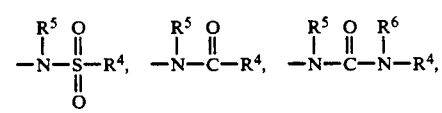

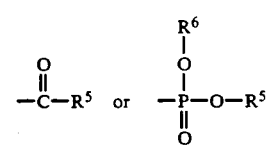

and
Y is oxygen.

5. A compound of claim 1, wherein the compound is:

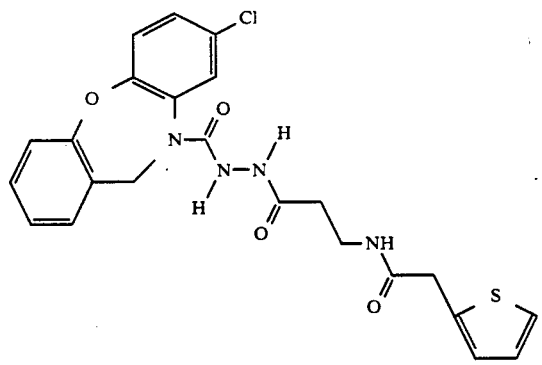

6. A compound of claim 1, wherein the compound is:

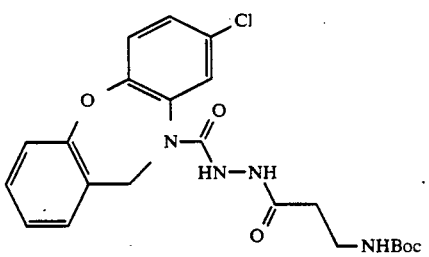

7. A compound of claim 1, wherein the compound is:

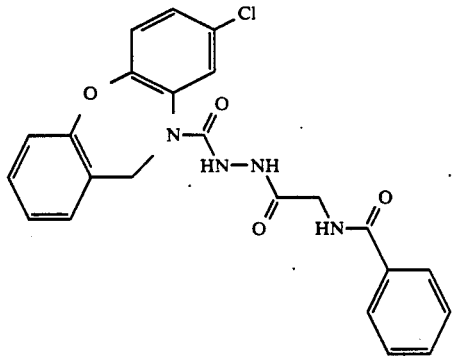

8. A compound of claim 1, wherein the compound is:

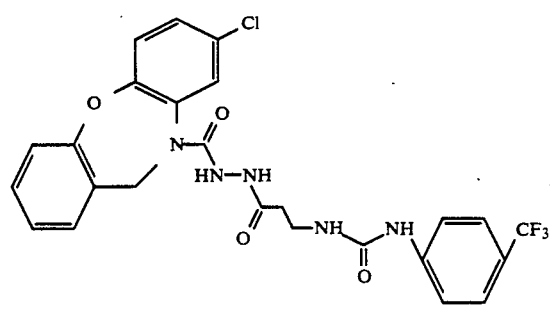

9. A compound of claim 1, wherein the compound is:

10. A compound of claim 1, wherein the compound is:
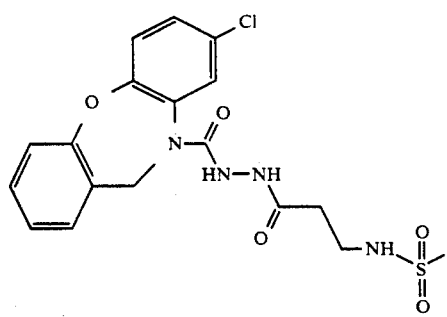
11. A compound of claim 1, wherein the compound is:
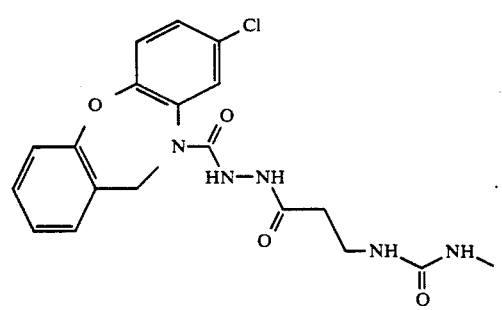
12. A compound of claim 1, wherein the compound is:
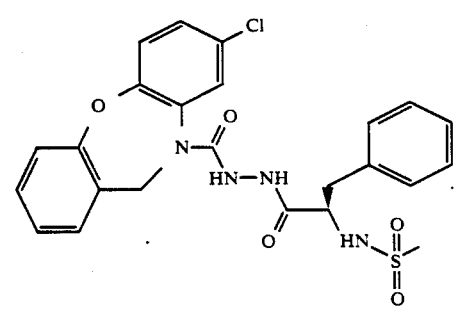
13. A compound of claim 1, wherein the compound is:
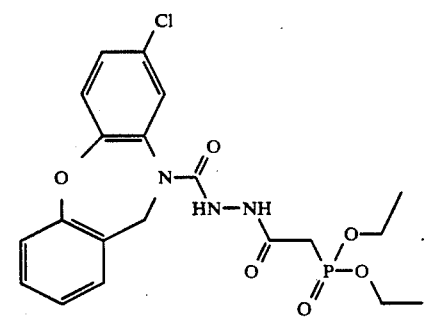
14. A compound of claim 1, wherein the compound is:
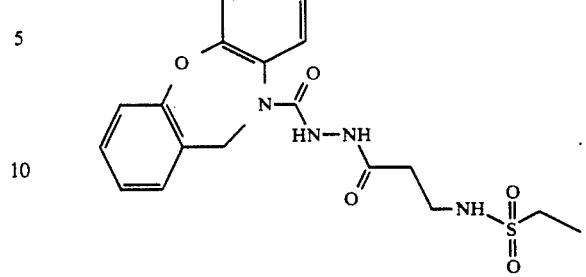
15. A compound of claim 1, wherein the compound is:
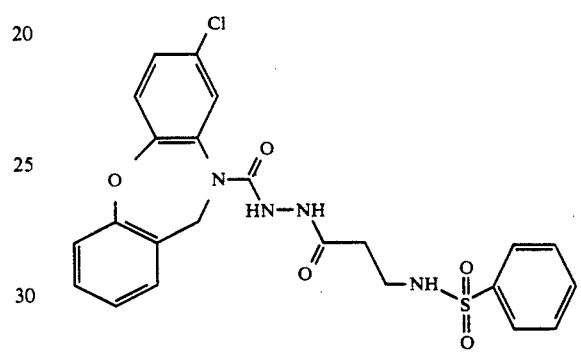
16. A compound of claim 1, wherein the compound is:
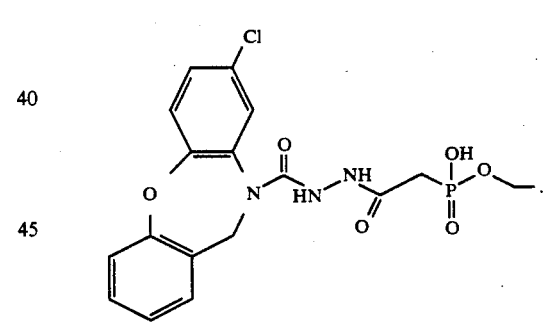
17. A compound of claim 1, wherein the compound is:
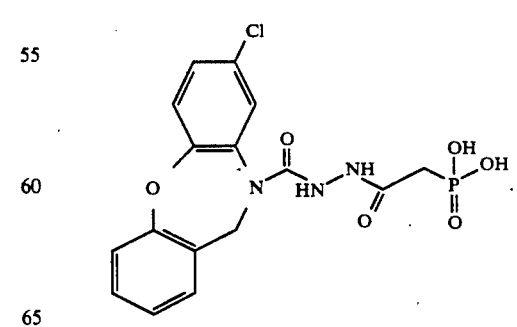

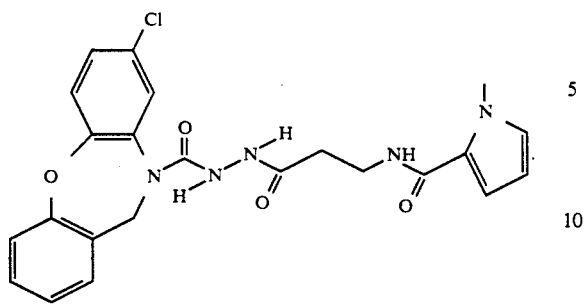
18. A compound of claim 1, wherein the compound is:
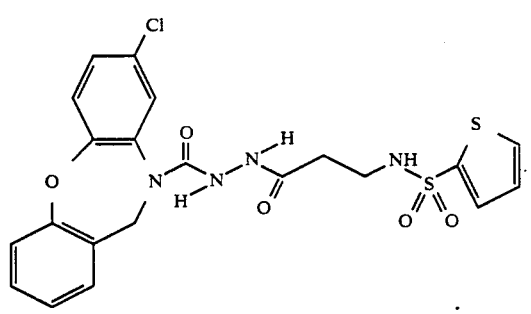
19. A compound of claim 1, wherein the compound is:
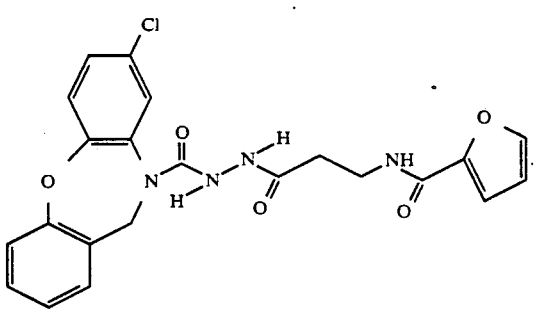
20. A compound of claim 1, wherein the compound is:
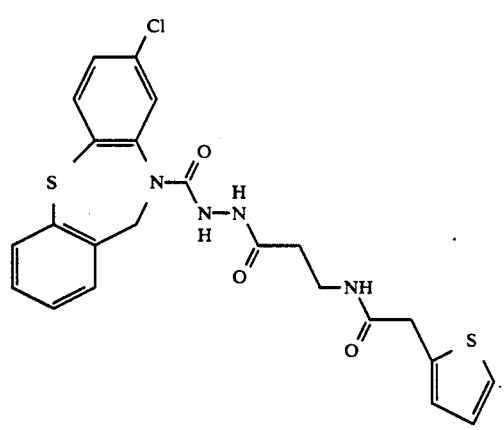
21. A compound of claim 1, wherein the compound is:
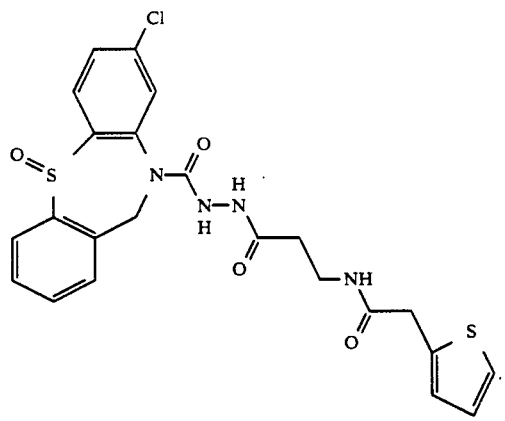
22. A compound of claim 1, wherein the compound is:
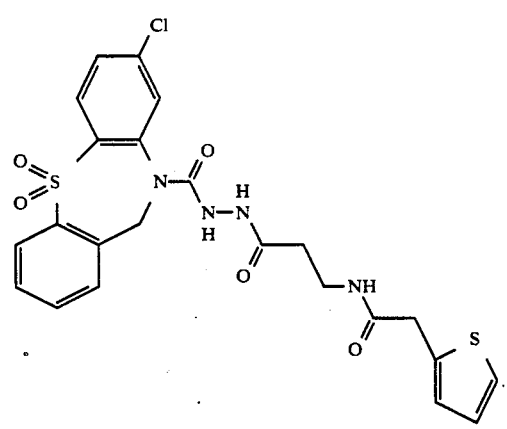
23. A compound of claim 1, wherein the compound is:
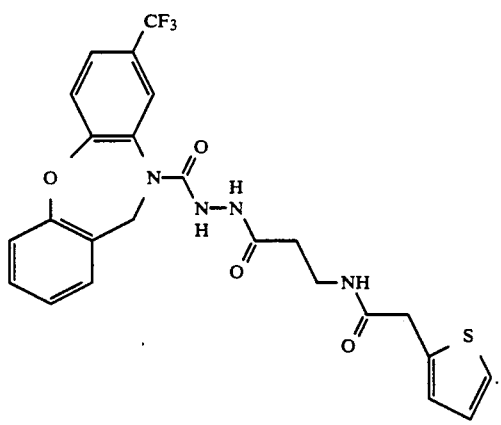
24. A compound of claim 1, wherein the compound is:

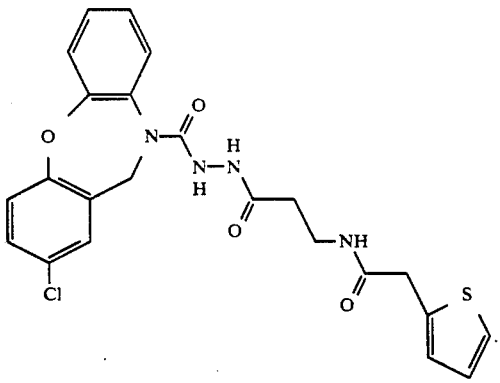

25. A pharmaceutical composition comprising a pharmaceutically-acceptable carrier and a therapeutically-effective amount of a compound of claim 1.

26. The pharmaceutical composition of claim 25 wherein the compound is selected from the group consisting of:

8-chlorodibenz[b,f][1,4]oxazepine-10(11H)-carboxylic acid, 2-[1-oxo-3-[(2-thienylacetyl)amino]propyl]hydrazide;

8-chlorodibenz[b,f][1,4]oxazepine-10(11H)-carboxylic acid, 2-[3-[[(1,1-dimethylethoxy)carbonyl]amino]-1-oxopropyl]hydrazide;

8-chlorodibenz[b,f][1,4]oxazepine-10(11H)-carboxylic acid, 2-[(benzoylamino)acetyl]hydrazide;

8-chlorodibenz[b,f][1,4]oxazepine-10(11H)-carboxylic acid, 2-[1-oxo-3-[[[[(4-trifluoromethyl)phenyl]amino]carbonyl]-amino]propyl]hydrazide;

8-chlorodibenz[b,f][1,4]oxazepine-10(11H)-carboxylic acid, 2-[3-[(methylsulfonyl)amino]-1-oxopropyl]hydrazide;

8-chlorodibenz[b,f][1,4]oxazepine-10(11H)-carboxylic acid, 2-[3-[[(methylamino)carbonyl]amino]-1-oxopropyl]hydrazide;

8-chlorodibenz[b,f][1,4]oxazepine-10(11H)-carboxylic acid, 2-[2-[(methylsulfonyl)amino]-1-oxo-3-phenyl]hydrazide;

8-chlorodibenz[b,f][1,4]oxazepine-10(11H)-carboxylic acid, 2-[(diethoxyphosphinyl)acetyl]hydrazide;

8-chlorodibenz[b,f][1,4]oxazepine-10(11H)-carboxylic acid, 2-[3-[(ethylsulfonyl)amino]-1-oxopropyl]hydrazide;

8-chlorodibenz[b,f][1,4]oxazepine-10(11H)-carboxylic acid, 2-[1-oxo-3-[(phenylsulfonyl)amino]propyl]hydrazide;

8-chlorodibenz[b,f][1,4]oxazepine-10(11H)-carboxylic acid, 2-[(ethoxyhydroxyphosphinyl)acetyl]hydrazide;

8-chlorodibenz[b,f][1,4]oxazepine-10(11H)-carboxylic acid, 2-(phosphonoacetyl)hydrazide;

8-chlorodibenz[b,f][1,4]oxazepine-10(11H)-carboxylic acid, 2-[3-[[(1-methyl-2-pyrrolyl)carbonyl]amino]-1-oxopropyl]hydrazide;

8-chlorodibenz[b,f][1,4]oxazepine-10(11H)-carboxylic acid, 2-[1-oxo-3-[(2-thienylacetyl)amino]propyl]hydrazide; and 8-chlorodibenz[b,f][1,4]oxazepine-10(11H)-carboxylic acid, 2-[3-[(2-furanylcarbonyl)amino]-1-oxopropyl]hydrazide.

27. A method for treating pain in a mammal comprising administering to said mammal a therapeutically-effective amount of a compound of claim 1.

28. The method of claim 27 wherein the compound is selected from the group consisting of:

8-chlorodibenz[b,f][1,4; ]oxazepine-10-(11H)-carboxylic acid, 2-[1-oxo-3-[(2-thienylacetyl)amino]propyl]hydrazide;

8-chlorodibenz[b,f][1,4; ]oxazepine-10-(11H)-carboxylic acid, 2-[3-[(1,1-dimethylethoxy)carbonyl]amino]-1-oxopropyl]hydrazide;

8-chlorodibenz[b,f][1,4]oxazepine-10(11H)-carboxylic acid, 2-[(benzoylamino)acetyl]hydrazide;

8-chlorodibenz[b,f][1,4]oxazepine-10(11H)-carboxylic acid, 2-[3-[(methylsulfonyl)amino]-1-oxopropyl]hydrazide;

8-chlorodibenz[b,f][1,4]oxazepine-10(11H)-carboxylic acid, 2-[3-[[(methylamino)carbonyl]amino]-1-oxopropyl]hydrazide;

8-chlorodibenz[b,f][1,4]oxazepine-10(11H)-carboxylic acid, 2-[(diethoxyphosphinyl)acetyl]hydrazide;

8-chlorodibenz[b,f][1,4]oxazepine-10(11H)-carboxylic acid, 2-[(ethoxyhydroxyphosphinyl)acetyl]hydrazide;

8-chlorodibenz[b,f][1,4]oxazepine-10(11H)-carboxylic acid, 2-(phosphonoacetyl)hydrazide;

8-chlorodibenz[b,f][1,4]oxazepine-10(11H)-carboxylic acid, 2-[3-[[(1-methyl-2-pyrrolyl)carbonyl]amino]-1-oxopropyl]hydrazide; and 8-chlorodibenz[b,f][1,4]oxazepine-10(11H)-carboxylic acid, 2-[3-[(2-furanylcarbonyl)amino]-1-oxopropyl]hydrazide.

* * * * *

UNITED STATES PATENT AND TRADEMARK OFFICE
CERTIFICATE OF CORRECTION

PATENT NO. : 5,182,272    Page 1 of 9

DATED : January 26, 1993

INVENTOR(S) : Hallinan, et al.

It is certified that error appears in the above-identified patent and that said Letters Patent is hereby corrected as shown below:

Column 1, line 35, reading "NSA1DS)" should read -- NSAIDS) --.

Column 1, line 44, reading "Description of Related Art" should read -- (2) Description of Related Art --.

Column 1, line 47, reading "[1,4-]" should read -- [1,4] --.

Column 2, line 1, reading "10,11dihy-" should read -- 10,11-dihy- --.

Column 2, line 6, reading "patent Application publication" should read -- Patent Application Publication --.

Column 2, line 10, reading "patent Application publication" should read -- Patent Application Publication --.

Column 2, line 19, reading "prostaglandin" should read -- Prostaglandin --.

Column 2, line 26, reading "-1oxopentyl)" should read -- -1-oxopentyl) --.

Column 2, line 60, reading "potential" should read -- Potential --.

Column 3, line 23, reading "polymorphic" should read -- Polymorphic --.

Column 3, line 25, reading "infra-Red" should read -- Infra-Red --.

UNITED STATES PATENT AND TRADEMARK OFFICE
CERTIFICATE OF CORRECTION

PATENT NO. : 5,182,272

DATED : January 26, 1993

INVENTOR(S) : Hallinan, et al.

It is certified that error appears in the above-identified patent and that said Letters Patent is hereby corrected as shown below:

Column 3, line 52, reading "Sc-19220" should read -- SC-19220 --.

Column 4, line 7, reading "contractions" should read -- Contractions --.

Column 4, line 19, reading "PharmacoIogy" should read -- Pharmacology --.

Column 4, line 19, reading "(198)," should read -- (1988), --.

Column 4, line 20, reading "Sc-19220" should read -- SC-19220 --.

Column 4, line 32, reading "Sc-19220" should read -- SC-19220 --.

Column 4, line 34, reading "lnhibitory" should read -- Inhibitory --.

Column 4, line 46, reading "JournaI" should read -- Journal --.

Column 4, line 49, reading "subsoinioes" should read -- subspinipes --.

Column 6, line 29, reading "(phenyl," should read -- phenyl, --.

Column 6, line 31, reading "pyrrolyl)" should read -- pyrrolyl --.

UNITED STATES PATENT AND TRADEMARK OFFICE
CERTIFICATE OF CORRECTION

PATENT NO. : 5,182,272

DATED : January 26, 1993

INVENTOR(S) : Hallinan, et al.

It is certified that error appears in the above-identified patent and that said Letters Patent is hereby corrected as shown below:

Column 19, line 36, reading "1t" should read -- It --.

Column 20, line 40, reading "Well" should read -- well --.

Column 21, line 2, reading "[b.f]" should read -- [b,f] --.

Column 21, line 40, reading "[b.f]" should read -- [b,f] --.

Column 21, line 57, reading "for hours" should read -- for 2 hours --.

Column 22, line 12, reading "(D1EA)" should read -- (DIEA) --.

Column 22, line 40, reading "(HPLc)" should read -- (HPLC) --.

Column 23, line 29, reading "(o.5 mmol)" should read -- (0.5 mmol) --.

Column 23, line 33, reading "Was" should read -- was --.

Column 23, line 55, reading "NaoH" should read -- NaOH --.

Column 23, line 55, reading "(t-BuoH)" should read -- (t-BuOH) --.

Column 23, line 60, reading "EtoAc." should read -- EtOAc. --.

Column 24, line 3, reading "[1.4]" should read -- [1,4] --.

Column 24, line 5, reading "2-(3-" should read -- 2-[(3- --.

Column 24, line 27, reading "D1EA" should read -- DIEA --.

UNITED STATES PATENT AND TRADEMARK OFFICE
CERTIFICATE OF CORRECTION

PATENT NO. : 5,182,272

DATED : January 26, 1993

INVENTOR(S) : Hallinan, et al.

It is certified that error appears in the above-identified patent and that said Letters Patent is hereby corrected as shown below:

Column 24, line 31, reading "EtoAc" should read -- EtOAc --.

Column 24, line 42, reading "Cl 0.75" should read -- Cl·0.75 --.

Column 25, line 5, reading "Cl 0.1" should read -- Cl·0.1 --.

Column 25, line 6, reading "c," should read -- C, --.

Column 25, line 40, reading "Cl 0.9 HCl 1.5" should read -- Cl·0.9 HCl·1.5 --.

Column 25, line 64, reading "i mmol)" should read -- 1 mmol --.

Column 26, line 32, reading "-i-oxopropyl]" should read -- 1-oxopropyl] --.

Column 27, line 37, reading "Cl 0.4" should read -- Cl·0.4 --.

Column 28, line 24, reading "I6 hours" should read -- 16 hours --.

Column 28, line 36, reading "2-[(methylsulfonyl)" should read -- 2-[2-[(methylsulfonyl) --.

UNITED STATES PATENT AND TRADEMARK OFFICE
CERTIFICATE OF CORRECTION

PATENT NO. : 5,182,272
DATED : January 26, 1993
INVENTOR(S) : Hallinan, et al.

It is certified that error appears in the above-identified patent and that said Letters Patent is hereby corrected as shown below:

Column 28, line 40, represented by the formula reading

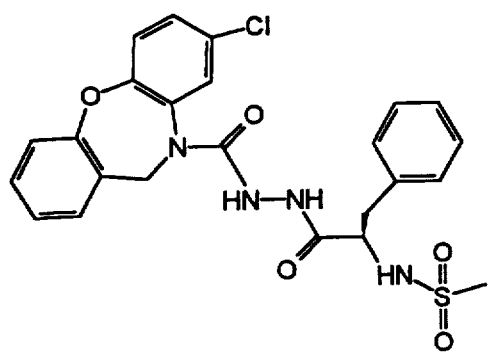     should read     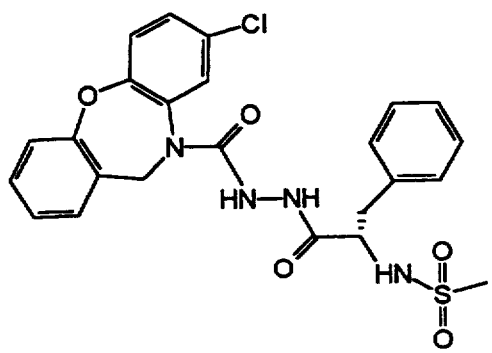

Column 28, line 56, reading "2,[2-((" should read -- 2,[2-[( --.

Column 29, line 38, reading "EtoAc" should read -- EtOAc --.

Column 29, line 48, reading "[b.f]" should read -- [b,f] --.

Column 31, line 5, reading "2-(diethoxyphosohinyl)" should read -- 2-[(diethoxyphosphinyl) --.

Column 31, line 25, reading "2bromoacetyl)" should read -- 2-(bromoacetyl) --.

Column 31, line 30, reading "Nal." should read -- NaI. --.

UNITED STATES PATENT AND TRADEMARK OFFICE
CERTIFICATE OF CORRECTION

PATENT NO. : 5,182,272

DATED : January 26, 1993

INVENTOR(S) : Hallinan, et al.

It is certified that error appears in the above-identified patent and that said Letters Patent is hereby corrected as shown below:

Column 31, line 65, reading "NO$_4$S 0.25" should read -- NO$_4$S·0.25 --.

Column 32, line 4, reading "8-clhorodibenz[b,fl" should read -- 8-chlorodibenz[b,f] --.

Column 32, line 5, reading "2-3-(ethylsulfonyl)aminol" should read -- 2-3-(ethylsulfonyl)amino] --.

Column 32, line 32, reading "[-b,f]" should read -- [b,f] --.

Column 32, line 41, reading "NO$_5$SCl 0.75" should read -- N$_4$O$_5$SCl·0.75 --.

Column 33, line 3, reading "[b,fl" should read -- [b,f] --.

Column 33, line 39, reading "I,3-" should read -- 1,3- --.

Column 34, line 36, reading "NaoH" should read -- NaOH --.

Column 34, line 37, reading "NaoH" should read -- NaOH --.

Column 34, line 40, reading "N HOl" should read -- N HCl --.

Column 34, line 49, reading "pCl 025" should read -- PCl·025 --.

Column 35, line 7, reading "Nal" should read -- NaI --.

Column 35, line 29, reading "oxazeopine" should read -- oxazepine --.

Column 36, line 5, reading "aminol" should read -- amino] --.

UNITED STATES PATENT AND TRADEMARK OFFICE
CERTIFICATE OF CORRECTION

PATENT NO. : 5,182,272
DATED : January 26, 1993
INVENTOR(S) : Hallinan, et al.

It is certified that error appears in the above-identified patent and that said Letters Patent is hereby corrected as shown below:

Column 36, line 37, reading "oxazeopine" should read -- oxazepine --.

Column 36, line 38, reading "acid. 2-[3-(2-" should read -- acid, 2-[3-[(2- --.

Column 36, line 65, reading "product" should read -- product. --.

Column 37, line 15, reading "i7g" should read -- 17g --.

Column 37, line 45, reading "thiazeoin" should read -- thiazepin --.

Column 38, line 47, reading "2-1-" should read -- 2-[1- --.

Column 38, line 47, reading "aminol" should read -- amino] --.

Column 39, line 61, reading "5oxodibenzo" should read -- 5-oxodibenzo --.

Column 40, line 2, reading "[b.f]" should read -- [b,f] --.

Column 40, line 31, reading "With" should read -- with --.

Column 41, line 35, reading "[b.fl" should read -- [b,f] --.

Column 42, line 47, reading "*proc.,*" should read -- *Proc.,* --.

Column 43, line 45, reading "b,f]" should read -- [b,f] --.

Column 44, line 4, reading "With" should read -- with --.

UNITED STATES PATENT AND TRADEMARK OFFICE
CERTIFICATE OF CORRECTION

PATENT NO. : 5,182,272
DATED : January 26, 1993
INVENTOR(S) : Hallinan, et al.

It is certified that error appears in the above-identified patent and that said Letters Patent is hereby corrected as shown below:

Column 44, line 9, reading "prostagland in" should read -- prostaglandin --.

Column 47, line 38, reading "aryl-substituted alkyl" should read -- aryl-substituted alkyl; --.

Column 49, line 40, represented by the formula reading

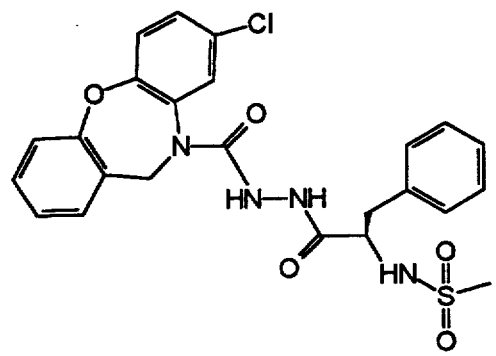

should read

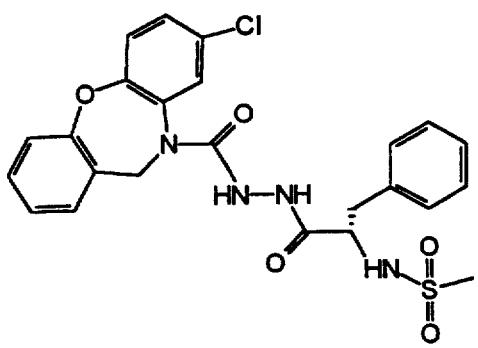

Column 54, line 23, reading "[1,4;]" should read -- [1,4] --.

Column 54, line 26, reading "[1,4;]" should read -- [1,4] --.

UNITED STATES PATENT AND TRADEMARK OFFICE
CERTIFICATE OF CORRECTION

PATENT NO. : 5,182,272
DATED : January 26, 1993
INVENTOR(S) : Hallinan, et al.

It is certified that error appears in the above-identified patent and that said Letters Patent is hereby corrected as shown below:

Column 54, line 27, reading "2-[3-" should read -- 2-[3-[ --.

Signed and Sealed this

Fourth Day of October, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,182,272
DATED : January 26, 1993
INVENTOR(S) : E. Ann Hallinan, et al It is certified that error appears in the above-indentified patent and that said Letters Patent is hereby corrected as shown below:

Column 4, line 4, reading "lndomethacin" should read -- Indomethacin--

Column 31, line 35, reading "2bromoacetyl)" should read -- 2-(bromoacetyl)--

Signed and Sealed this

Eighteenth Day of October, 1994

Attest:

BRUCE LEHMAN

Attesting Officer    Commissioner of Patents and Trademarks